US012324637B2

(12) United States Patent
DiMaio et al.

(10) Patent No.: US 12,324,637 B2
(45) Date of Patent: Jun. 10, 2025

(54) BASE POSITIONING SYSTEM FOR A CONTROLLABLE ARM AND RELATED METHODS

(71) Applicant: Intuitive Surgical Operations, Inc., Sunnyvale, CA (US)

(72) Inventors: Simon Peter DiMaio, San Carlos, CA (US); Nicholas Leo Bernstein, Cary, NC (US); Paul Millman, San Jose, CA (US); Dinesh Rabindran, Cupertino, CA (US); Alec Paul Robertson, Palo Alto, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 893 days.

(21) Appl. No.: 17/494,300

(22) Filed: Oct. 5, 2021

(65) Prior Publication Data

US 2022/0022980 A1 Jan. 27, 2022

Related U.S. Application Data

(63) Continuation of application No. 16/331,460, filed as application No. PCT/US2017/050526 on Sep. 7, 2017, now Pat. No. 11,166,770.

(Continued)

(51) Int. Cl.
*A61B 34/00* (2016.01)
*A61B 34/30* (2016.01)
(Continued)

(52) U.S. Cl.
CPC .............. *A61B 34/30* (2016.02); *A61B 34/00* (2016.02); *A61B 50/13* (2016.02); *A61B 90/03* (2016.02);
(Continued)

(58) Field of Classification Search
USPC .............................. 606/1, 130; 700/245–264
See application file for complete search history.

(56) References Cited

U.S. PATENT DOCUMENTS

| 4,547,119 A | 10/1985 | Chance et al. |
| 5,796,229 A | 8/1998 | Akeel |

(Continued)

FOREIGN PATENT DOCUMENTS

| CA | 2896381 A1 * | 9/2014 | ......... A61B 17/3421 |
| CN | 102458295 A | 5/2012 | |

(Continued)

OTHER PUBLICATIONS

Office Action for Chinese Application No. CN20178038163, mailed Jul. 25, 2022, 18 pages.

(Continued)

*Primary Examiner* — Jonathan L Sample
(74) *Attorney, Agent, or Firm* — MARSHALL, GERSTEIN & BORUN LLP

(57) ABSTRACT

A robotic system includes a base movable relative to a floor surface and a controllable arm extending from the base. The arm is configured to support and move a tool. The arm has a powered joint operable to position and/or orient a distal portion of the arm. The robotic system further includes a processor coupled to the powered joint and configured to drive the powered joint to reposition the base while the position and/or orientation of the distal portion of the arm is maintained.

16 Claims, 14 Drawing Sheets

Related U.S. Application Data

(60) Provisional application No. 62/396,714, filed on Sep. 19, 2016.

(51) Int. Cl.
    *A61B 50/13*      (2016.01)
    *A61B 90/00*      (2016.01)
    *A61B 90/50*      (2016.01)
    *B25J 9/12*      (2006.01)
    *B25J 9/16*      (2006.01)
    *A61B 34/20*      (2016.01)

(52) U.S. Cl.
    CPC .............. *A61B 90/50* (2016.02); *B25J 9/126* (2013.01); *B25J 9/1664* (2013.01); *B25J 9/1689* (2013.01); *A61B 2034/2048* (2016.02); *A61B 2034/2059* (2016.02)

(56) References Cited

U.S. PATENT DOCUMENTS

| | | | |
|---|---|---|---|
| 5,835,693 A | | 11/1998 | Lynch et al. |
| 6,115,053 A | | 9/2000 | Perlin |
| 6,456,901 B1 | | 9/2002 | Xi et al. |
| 6,589,195 B1 | | 7/2003 | Schwenn et al. |
| 6,643,563 B2 | | 11/2003 | Hosek et al. |
| 6,789,755 B1 | * | 9/2004 | Mack ........................ A01K 1/01 239/587.5 |
| 6,991,627 B2 | | 1/2006 | Madhani et al. |
| 7,813,836 B2 | | 10/2010 | Wang et al. |
| 7,996,110 B2 | | 8/2011 | Lipow et al. |
| 8,006,332 B2 | | 8/2011 | Lemire et al. |
| 8,556,808 B2 | | 10/2013 | Miles et al. |
| 8,965,579 B2 | | 2/2015 | Wang et al. |
| 9,855,655 B2 | | 1/2018 | Inutake et al. |
| 10,059,000 B2 | | 8/2018 | Herzog et al. |
| 10,478,362 B2 | | 11/2019 | Gockeritz et al. |
| 10,575,908 B2 | * | 3/2020 | Schena .................. A61B 34/37 |
| 10,707,636 B2 | | 7/2020 | Yamamoto |
| 10,959,783 B2 | * | 3/2021 | Gregerson ............. A61B 46/10 |
| 11,166,770 B2 | * | 11/2021 | DiMaio .................. A61B 34/00 |
| 2002/0045905 A1 | | 4/2002 | Gerbi et al. |
| 2003/0167103 A1 | | 9/2003 | Tang et al. |
| 2003/0225479 A1 | | 12/2003 | Waled |
| 2004/0249508 A1 | | 12/2004 | Suita et al. |
| 2004/0254679 A1 | | 12/2004 | Nagasaka |
| 2005/0154431 A1 | * | 7/2005 | Quistgaard .......... A61B 5/6843 607/96 |
| 2006/0149418 A1 | * | 7/2006 | Anvari .................. A61B 34/74 700/245 |
| 2007/0013336 A1 | | 1/2007 | Nowlin et al. |
| 2007/0142968 A1 | | 6/2007 | Prisco et al. |
| 2007/0255454 A1 | | 11/2007 | Dariush |
| 2007/0287884 A1 | | 12/2007 | Schena |
| 2008/0065105 A1 | | 3/2008 | Larkin et al. |
| 2008/0065109 A1 | | 3/2008 | Larkin |
| 2008/0161830 A1 | * | 7/2008 | Sutherland ............. A61B 34/74 606/130 |
| 2008/0188986 A1 | | 8/2008 | Hoppe |
| 2008/0287963 A1 | | 11/2008 | Rogers et al. |
| 2009/0024142 A1 | | 1/2009 | Ruiz Morales |
| 2009/0192524 A1 | * | 7/2009 | Itkowitz ................. B25J 9/1689 606/130 |
| 2009/0228145 A1 | | 9/2009 | Hodgson et al. |
| 2009/0326553 A1 | | 12/2009 | Mustufa et al. |
| 2009/0326711 A1 | | 12/2009 | Chang et al. |
| 2010/0063630 A1 | | 3/2010 | Sutherland et al. |
| 2011/0040404 A1 | | 2/2011 | Diolaiti et al. |
| 2011/0071675 A1 | | 3/2011 | Wells et al. |
| 2011/0268548 A1 | | 11/2011 | Doll |
| 2012/0205049 A1 | | 8/2012 | Weber et al. |
| 2012/0239194 A1 | | 9/2012 | Kagawa |
| 2012/0290134 A1 | * | 11/2012 | Zhao ...................... A61B 34/37 901/47 |
| 2013/0190925 A1 | | 7/2013 | Miyoshi |
| 2013/0325031 A1 | * | 12/2013 | Schena .................. A61B 34/70 606/130 |
| 2014/0055489 A1 | * | 2/2014 | Itkowitz .................. G06T 11/40 345/633 |
| 2014/0350714 A1 | | 11/2014 | Kimura et al. |
| 2015/0100066 A1 | * | 4/2015 | Kostrzewski ...... A61B 17/1615 606/130 |
| 2015/0164504 A1 | | 6/2015 | Atkinson et al. |
| 2016/0135816 A1 | * | 5/2016 | Lavallee ................ B25J 9/0009 606/88 |
| 2016/0157942 A1 | * | 6/2016 | Gombert ................ A61B 34/30 606/130 |
| 2016/0184032 A1 | * | 6/2016 | Romo .................... B25J 13/085 901/46 |
| 2016/0199142 A1 | * | 7/2016 | Griffiths ................ A61B 34/30 606/130 |
| 2019/0216555 A1 | * | 7/2019 | DiMaio .................. B25J 9/1664 |
| 2022/0022980 A1 | * | 1/2022 | DiMaio .................. A61B 50/13 |

FOREIGN PATENT DOCUMENTS

| | | |
|---|---|---|
| CN | 105050527 A | 11/2015 |
| KR | 101550451 B1 | 9/2015 |
| KR | 20160010426 A | 1/2016 |
| WO | WO-2013181507 A1 | 12/2013 |
| WO | WO-2014028699 A1 | 2/2014 |
| WO | WO-2015142907 A1 | 9/2015 |
| WO | WO-2015142947 A1 | 9/2015 |
| WO | WO-2016161444 A1 | 10/2016 |

OTHER PUBLICATIONS

Extended European Search Report for Application No. EP17851345.3 mailed on Apr. 21, 2020, 09 pages.

International Search Report and Written Opinion for Application No. PCT/US2017/050526, mailed on Jan. 8, 2018, 10 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

BASE POSITIONING SYSTEM FOR A CONTROLLABLE ARM AND RELATED METHODS

CROSS-REFERENCE TO RELATED APPLICATIONS

This application is a continuation of and claims the benefit of priority to U.S. patent application Ser. No. 16/331,460, filed Mar. 7, 2019, which is a U.S. National Stage Application under 35 U.S.C. § 371 and claims the benefit of International Patent Application No. PCT/US2017/050526, filed on Sep. 7, 2017, which claims the benefit of priority to U.S. Provisional Patent Application No. 62/396,714, filed on Sep. 19, 2016, the disclosures of which are incorporated herein by reference in their entirety.

TECHNICAL FIELD

This specification relates to a base positioning system for a remotely controllable arm, and more specifically, for a remotely controllable arm of a robotic system.

BACKGROUND

Robotic systems can include robotic arms to manipulate instruments for performing a task at a work site. The robotic arm can include two or more links coupled together by one or more joints. The joints can be active joints that are actively controlled. The joints can also be passive joints that comply with movement of the active joints as the active joints are actively controlled. Such active and passive joints may be revolute or prismatic joints. The configuration of the robotic arm may then be determined by the positions of the joints, the structure of the robotic arm, and the coupling of the links.

Robotic systems include industrial and recreational robotic systems. Robotic systems also include medical robotic systems used in procedures for diagnosis, non-surgical treatment, surgical treatment, etc. As a specific example, robotic systems include minimally invasive, robotic telesurgical systems in which a surgeon can operate on a patient from a bedside location or a remote location. Telesurgery refers generally to surgery performed using surgical systems where the surgeon uses some form of remote control, e.g., a servomechanism, to manipulate surgical instrument movements rather than directly holding and moving the instruments by hand. A robotic surgical system usable for telesurgery can include a remotely controllable robotic arm. Operators can remotely control motion of the remotely controllable robotic arm. Operators can also manually move pieces of the robotic surgical system into positions within a surgical environment. For example, a surgeon, a surgical assistant, or other operator can push or pull the equipment by hand such that the equipment moves along a floor surface of the surgical environment.

SUMMARY

In one aspect, a surgical system includes a base movable relative to a floor surface and a remotely controllable arm extending from the base and configured to support and move a surgical tool. The arm has a powered joint operable to position and/or orient a distal portion of the arm. The surgical system further includes a processor coupled to the powered joint and configured to drive the powered joint to reposition the base while the position and/or orientation of the distal portion of the arm is externally maintained.

In another aspect, a method includes determining an optimality score based on a pose of a remotely controllable arm of a surgical system. The method also includes driving a powered joint to reposition a base of the remotely controllable arm such that the optimality score is greater than a threshold score. The method further includes driving the powered joint, based on a remote operator input, to cause movement of the remotely controllable arm to perform a surgical operation while the optimality score is greater than the threshold score.

In another aspect, a method of operating a robotic system including a robotic arm extending from a base and supporting a tool is featured. The method includes: determining, by a processor, a target base pose of the base; and driving a powered joint of the robot arm to move the base toward the target base pose while a position and/or orientation of a distal portion of the arm is externally maintained.

In yet another aspect, a non-transitory machine-readable medium includes a plurality of machine-readable instructions. These instructions, when executed by one or more processors associated with a robotic system, are adapted to cause the one or more processors to perform a method. The method may be any of the methods disclosed herein.

Certain aspects include one or more implementations described herein and elsewhere, including any appropriate combination of the implementations described below.

In some implementations, the processor is configured to operate the powered joint while the position and/or orientation of the distal portion of the remotely controllable arm is externally maintained relative to a reference. In some implementations, the reference is a reference point, such as a point corresponding to a location of an access port on a patient through which the surgical tool is inserted, or is to be inserted. In some implementations, the reference includes one or more reference directions but not a reference location; for example, the one or more reference directions may be based on the three-dimensional orientation of the distal portion immediately prior to a beginning of the repositioning process. In some implementations, the reference includes both a reference location and one or more reference directions when position and one or more orientation(s) are maintained. In some implementations, the reference includes a full reference frame sufficient to define location and orientation in three-dimensional space.

In some implementations, the position and/or orientation of the distal portion is externally maintained by maintaining a position and/or orientation of a cannula or tool or other device held by the arm. In some implementations, the processor is further configured to drive the powered joint to move the distal portion of the arm while a position and/or orientation of the base is maintained. In some implementations, the processor is further configured to slow or stop repositioning the base in response a determination that the position and/or orientation of the distal portion is not maintained while the base is repositioned.

In some implementations, the surgical system further includes a cart supported on the floor surface. In some cases, the surgical system further includes a setup assembly including a passive joint connecting the cart to the base. In some cases, the processor is configured to reposition the base while the cart is movable relative to the floor surface or the base is movable relative to the cart. In some implementations, the surgical system further includes a setup assembly for attaching the base to a table. In some cases, the processor is configured to drive the powered joint to reposition the base while the base is movable relative to the table.

In some implementations, the arm further includes a second powered joint connected to the powered joint by a linkage, and the second powered joint is operable to move the distal portion. In some cases, the processor is configured to drive both the powered joint and the second powered joint to reposition the base while the position of the distal portion of the arm is externally maintained.

In some implementations, the surgical system further includes a sensor configured to generate a signal in response to detecting that the distal portion is substantially fixed relative to an appropriate reference, such as relative to a reference point, to one or more reference directions, or to a reference frame. The processor is, for example, configured to drive the powered joint to reposition the base in response to the signal.

In some implementations, the surgical system further includes a selectively releasable joint connecting the arm to the base. The processor is configured to lock the selectively releasable joint when the selectively releasable joint has reached a desired position. In some cases, the processor is configured to drive the powered joint to reposition the selectively releasable joint to the desired position based on a predicted torque at the selectively releasable joint when the powered joint is driven to reposition the tool.

In some implementations, the surgical system further includes a selectively releasable joint connecting the arm to the base. The processor is, for example, configured to drive the powered joint and to selectively release the selectively releasable joint to reposition the base.

In some implementations, the surgical system further includes a connection joint connecting the arm to the base. The processor is, for example, configured to drive the powered joint to reposition the connection joint toward a desired position.

In some implementations, the processor is configured to inhibit motion of the base in response to determining that the base is within an optimal base location envelope relative to an appropriate reference such as the floor surface.

In some implementations, the surgical system further includes a setup assembly supporting the base above the floor surface. The setup assembly, for example, includes powered wheels to move the setup assembly relative to the floor surface. The processor is further configured to, for example, drive the powered wheels to reposition the base relative to the distal portion while the distal portion is positioned.

In some implementations, the surgical system further includes a sensor to generate a signal indicative of a position of the arm. The processor is, for example, configured to detect a manual demonstration of a desired range of motion of the arm based on the signal indicative of the position of the arm and to drive the powered joint to reposition the base based on the manual demonstration. In some cases, the processor is configured to activate an alert in response to detecting that the distal portion or surgical tool is unstable while driving the powered joint.

In some implementations, the surgical system further includes a plurality of sensors configured to generate signals indicative of positions of the base and the powered joint. The sensors, for example, include at least one of a proximity sensor, a force sensor, or a pressure sensor.

In some implementations, the processor is configured to drive the powered joint to reposition the base relative to an obstacle positioned above the floor surface.

In some implementations, the processor is further configured to control the arm to insert the tool into an access port of a patient to perform a surgical operation and to drive the powered joint to reposition the base while the tool is inserted into the access port and while the position and/or orientation of the surgical tool is externally maintained. In some cases, the reference includes a reference point corresponding to a location of the access port through which the tool is inserted.

In some implementations, the arm is a first arm configured to support and position a first surgical tool. The first arm has, for example, the powered joint movable to orient the first surgical tool with respect to a first reference. The surgical system further includes, for example, a second remotely controllable arm configurable to support and position a second surgical tool. The processor is, for example, configured to drive the powered joint of the first arm to reposition the base based on a pose of the first arm relative to a pose of the second arm while the position and/or orientation of the first surgical tool relative to the first reference is maintained. In some cases, the second arm extends from the base.

In some cases, the second arm has a powered joint operable to move the second surgical tool. The processor is configured, for example, to drive the powered joint of the second arm to reposition the base based on the pose of the first arm relative to the pose of the second arm while the position and/or orientation of a distal portion of the second arm is maintained.

In some cases, the second arm includes a selectively releasable passive joint. The processor is, for example, configured to drive the powered joint of the first arm and selectively release the selectively releasable passive joint to use reactive forces to move the passive joint.

In some cases, the base is a first base, and the surgical system further includes a second base connected to the second arm and movable relative to the first base.

In some implementations, the surgical system further includes a movable table configured to support a patient above the floor surface. The processor, for example, is configured to drive the movable table while maintaining the position and/or orientation of the distal portion of the arm. The movable table is, for example, connected to the base.

Advantages of the foregoing may include, but are not limited to, those described below and herein elsewhere. The processor can reposition the base such that the powered joint is moved relative to the base to a position that enables optimal use of the range of motion of the powered joint. In examples in which the arm includes joints in addition to the powered joint, the repositioning facilitated by the control the powered joint can move the base to positions relative to these joints to improve ranges of motion of these joints. Absent such repositioning of the base relative to the joints, the base may be in a position along the floor surface that does not allow the joints to move through ranges of motion necessary to perform a specific surgical procedure.

Driving the powered joint to reposition the base can also expedite the repositioning process for the base. For example, errors that may occur when an operator manually repositions the base can be avoided through the use of the powered joint to move the base. Furthermore, because the processor can control the powered joint while the surgical tool's position and/or orientation relative to the reference is maintained, the processor can reposition the base without affecting the position of the surgical tool. For example, the surgical tool can be positioned or placed into an access port on the patient before the repositioning of the base. The subsequent step of positioning the base can be decoupled from the step of placing the surgical tool, as the positioning of the base occurs while the position and/or orientation of the surgical tool is maintained. The surgical tool therefore does not have to be repositioned after the base is repositioned.

Although the specific examples presented in this disclosure often discuss surgical examples, the techniques disclosed are also applicable to non-surgical use. For example, they may be used with and improve general or industrial robotic operations, such as those use in manipulating work pieces. These techniques may also be used with and improve medical robotic operations for diagnoses and non-surgical treatment.

Further, although the specific examples presented in this disclosure often discuss teleoperational robotic systems and remotely controllable arms, the techniques disclosed are also applicable to robotic systems that are directly and manually moved by operators, in part or in whole. For example, these techniques can be applied to robotic systems designed to help steady a tool held by the robotic arm while the tool is manipulated hand of an operator. As another example, any of the controllable arms discussed herein may be configured to allow direct manipulation, and accept operator instruction through input directly applied to a link or a joint of the manipulator.

The details of one or more implementations of the subject matter described in this specification are set forth in the accompanying drawings and the description below. Other potential features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
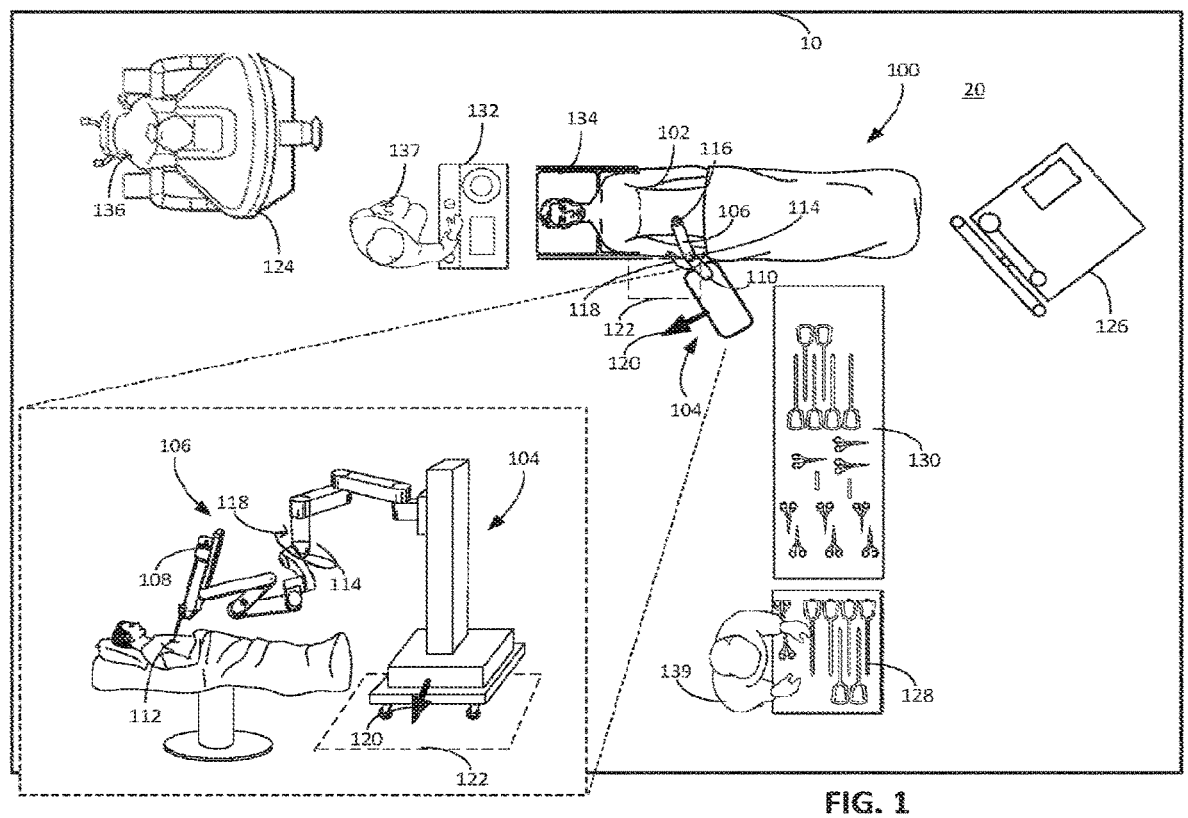
FIG. 1 is a top view of a surgical system in a surgical environment.

Starting with a surgical example, operator or operators (e.g., one or more of surgeons, surgical assistants, nurses, technicians, and other medical practitioners) can operate a surgical system 100, depicted in FIG. 1, to perform a surgery on a patient 102 in a surgical environment 10. The operators can interact with the surgical system 100 to operate a surgical manipulator assembly 104 including a remotely controllable arm 106 to perform the surgery. A surgical tool 108 mounted on the remotely controllable arm 106 can be operated to perform the surgery on the patient 102 when the remotely controllable arm 106 is manipulated. The remotely controllable arm 106 includes a base 110 supported above a floor surface 20 of the surgical environment 10. The base 110 supports the remotely controllable arm 106 above the floor surface 20 such that, during a surgical operation in which the remotely controllable arm 106 is manipulated to perform the surgery, the remotely controllable arm 106 moves about the surgical environment 10 above the floor surface 20 relative to the base 110. The surgical tool 108 and the base 110 can be positioned or repositioned before the surgery is performed such that the surgical tool 108 and the remotely controllable arm 106 are optimally positioned for surgery.

"Reposition" is used with the base herein to indicate changing the position, the orientation, or both the position and orientation of the base.

During the repositioning of the base 110, a distal portion of the remotely controllable arm 106 (or an item supported by the remotely controllable arm, such as a cannula or a surgical tool 108 mounted on the remotely controllable arm 106 and extending distally relative to the remotely controllable arm) can be externally maintained in a desired position and/or orientation within the surgical environment 10. For example, the desired position and/or orientation may be referenced to a frame of reference, and held stationary relative to that frame of reference. Example frames of reference include coordinate frames attached to specific patient tissue or anatomical feature, to a surface supporting the patient, to the floor surface, to the surgical environment, etc.

"And/or" is used herein to indicate either or both of two stated possibilities. For example, "a position and/or orientation" is used to indicate a position, an orientation, or a combination of both position and orientation parameters.

The position is maintained when the position is kept within an acceptable range of position changes. For example, in some implementations, the acceptable range of position changes is zero, and maintained the position involves keeping the position completely unchanged. In some implementations, the acceptable range of position changes is nonzero, and is based on the limits of the system's design; the position is maintained as close to unchanging as possible given mechanical, electrical, and computational tolerances and errors. In some implementations, the acceptable range of position changes is nonzero, and includes bounds based on operating conditions. For example, in some cases, the acceptable range of position changes is on the order of millimeters or centimeters, and is set to avoid damage to a work piece or human tissue. In some cases, the acceptable range of position changes is larger. In some cases, the acceptable range of position changes differ among different translational degrees of freedom.

Similarly, the orientation is maintained when the orientation is kept within an acceptable range of orientation changes. In various implementations, the acceptable range of orientation changes may be zero, may be a minimal amount limited by system performance, may be less than a degree or multiple degrees or larger, based on performance conditions such as avoiding damage to a work piece or human tissue, and the like. In some cases, the acceptable range of orientation changes differ among different rotational degrees of freedom.

In some implementations, the distal portion of the arm that is maintained in position and/or orientation may include part or all of a distal link of the arm. For example, the distal portion that is maintained may include a distal end of the distal link, may include a portion of the distal link configured to be adjacent an access port during operation, may include a portion of the distal link that couples to a device that mounts to the arm, such as a tool or a cannula, etc.

Similarly, a tool or a cannula that is maintained in position and/or orientation may include part or all of a tool or cannula. For example, a tool or a cannula can be considered to be maintained in position and/or orientation when the position and/or orientation of a particular part of the tool or cannula is maintained. In some cases, a tool or a cannula is maintained in position and/or orientation by maintaining the position and/or orientation of a distal end of the tool or cannula, of a portion of the tool or cannula adjacent to an access port, if a portion of the tool or cannula that coincides with a remote center of rotation of the tool or cannula, etc.

In some implementations, a desired position may be relative to a reference point in the surgical environment 10. For example, the desired position of distal portion of the remotely controllable arm (or an item supported by the remotely controllable arm) can correspond to a pose in which a cannula or a surgical tool or other surgical device would be (or is already) inserted into an access port in the patient 102. An example access port in the patient 102 is a minimally invasive aperture on the patient 102. In some cases, an operator places the remotely controllable arm 106 in a desired position before the repositioning of the base 110 occurs. Alternatively, the operator places a device mounted to the remotely controllable arm 106 in a desired position before the repositioning of the base 110 occurs. Examples of devices that may be mounted to the remotely controllable arm 106 includes the surgical tool 108 or cannula or other surgical device. During the repositioning of the base 110, the end-effector remains in the desired position with respect to the reference point.

The system 100 may move the base 110 toward an optimal base location envelope 122 during the repositioning. The optimal base location envelope 122, for example, corresponds to a range of three-dimensional positions for the base 110 within the surgical environment 10. When the base 110 is within the optimal base location envelope 122, the remotely controllable arm 106 can be positioned and oriented such that a surgical tool 108 mounted to the remotely controllable arm 106 can easily access areas of the anatomy of the patient 102 relevant to the surgical procedure to be performed or being performed.

To reposition the base 110, one or more processors of the surgical system 100 can drive a powered joint of the remotely controllable arm 106 by selectively activating one or more actuators that move the powered jointed. The driven motion of the powered joint can backdrive and thus move the base 110. In some cases, this backdriving of the base 110 is achieved with only the driven motion of the powered joint, and no motion of any other joint(s) of the arm 106. In some cases, this backdriving of the base 110 is achieved with the driven motion of the powered joint complemented by additional driven motion of one or more other powered joint(s) of the arm 106. In some cases, this backdriving of the base 110 is achieved with the driven motion(s) coupled with backdriven motion of one or more other joint(s) of the arm 106.

A pose of the distal portion of a manipulator arm (or of the item held by the manipulator arm) can include a position, an orientation, or any combination of position and orientation parameters, of the distal portion (or of the item). Thus, although the specific examples presented in this disclosure often discuss for simplicity maintaining the position of a distal portion of a controllable arm, the techniques described herein are usable in other respects as well. For example, they may be used to maintain a position, an orientation, or a combination of position and orientation parameters for a distal portion of a controllable arm, or for an item supported by the controllable arm (such as a cannula or tool or other device).

The position and/or orientation may be maintained relative to any appropriate reference. In some implementations, the reference includes a reference point, one or more reference directions, or a reference frame. An example reference point is a point corresponding to a location of an access port on a patient 102 through which the surgical tool is inserted, or is to be inserted. A single point without orientation information can be sufficient in implementations where only position is maintained. In some implementations, the reference includes one or more reference directions but not a reference location; for example, the one or more reference directions may be based on the three-dimensional orientation of the distal portion immediately prior to a beginning of the repositioning process. A set of direction(s) without a reference location can be sufficient in implementations where only the orientation(s) corresponding to the set of direction(s) are maintained. In some implementations, the reference includes both a reference location and one or more reference directions when position and one or more orientation(s) are maintained. In some implementations, the reference includes a full reference frame sufficient to define location and orientation in three-dimensional space.

As a specific example, and referring to FIG. 1, after the surgical tool 108 is positioned within an access port 112 on the patient 102, a powered joint 114 of the remotely controllable arm 106 can be driven to position the base 110 within the surgical environment 10. When the surgical tool 108 is inserted into the access port 112, the tissue of the patient 102 may provide a sufficient reaction force to torque exerted by the powered joint 114 to externally maintain the surgical tool 108 and the arm 106 as fixed in position and/or orientation relative to a reference within the surgical environment 10 while the base 110 is repositioned. Alternatively, the operator places a distal portion of the remotely controllable arm 106 (or an item mounted to the remotely controllable arm 106) in a desired position before the repositioning of the base 110 occurs. During the repositioning, the distal portion (or the item mounted to the arm 106) is externally maintained by the operator in the desired position and/or orientation with respect to the reference. Other techniques for externally maintaining the position and/or orientation of the distal portion are described below. Examples of references include reference points, reference directions, and reference frames that correspond to the floor surface, the surgical environment 10, an anatomical feature or tissue of the patient 102, a part of the arm 106 prior to repositioning, etc. In FIG. 1, an example reference point 116 is shown that corresponds to the position of the access port 112. In some implementations, the powered joint 114 of the remotely controllable arm 106 is driven to reposition the base 110 before a surgical operation is performed. The same powered joint 114, in some cases, is driven during the surgical operation to manipulate the surgical tool 108.

The powered joint 114 is, for example, driven in a drive direction 118 while the surgical tool 108 is fixed relative the reference (such as a reference including reference point 116). Because the surgical tool 108 is fixed, the movement of the powered joint 114 in the drive direction 118 causes the base 110 to move in a repositioning direction 120. As a result, when the powered joint 114 is driven, the base 110 is backdriven and thereby moves within the surgical environment 10. Backdriving the base 110 through selective activation of the powered joint 114 causes the base 110 to be repositioned toward an optimal base location envelope 122. The optimal base location envelope 122, for example, corresponds to a range of three-dimensional positions for the base 110 within the surgical environment 10 considered optimal for the base 110. The use of the powered joint 114 to drive the base 110 toward the optimal base location envelope 122 advantageously can enable the surgical tool 108 and the remotely controllable arm 106 to be optimally positioned and oriented to perform the surgery on the patient 102 when the positioning of the base 110 is complete.

Although the example discussed above shows the surgical tool 108 as mounted on the arm 106 and inserted into the patient 102, the above technique can also be used to reposition the base of a system without a mounted surgical tool, or with a mounted surgical tool that is not inserted into the patient. For example, a distal portion of the arm 106 (or an item held in the distal portion, such as a cannula or a surgical tool) may be externally maintained in position and/or orientation by any appropriate technique. Example external maintenance techniques include any one or combination of: patient tissue forces, operator applied forces, fixtures, other robotic arms, and other techniques different from driving the actuators or brakes of the arm 106. Because the distal portion is held in place directly, or indirectly through an intermediary such as an item mounted to the distal portion, the movement of the powered joint 114 in the drive direction 118 causes the base 110 to move in a repositioning direction 120. As a result, when the powered joint 114 is driven, the base 110 is backdriven and thereby moves within the surgical environment 10.

Example Surgical System

In the example of the surgical system 100 shown in FIG. 1, the powered joint 114, when driven, repositions the base 110 in the surgical environment 10. The surgical manipulator assembly 104 includes the remotely controllable arm 106 extending from the base 110. The base 110 is movable relative to the floor surface 20 toward an optimal pose, e.g., toward the optimal base location envelope 122. As described herein, in some implementations, the powered joint 114, when driven, causes the base 110 to move toward the optimal base location envelope 122. The base 110, in some cases, is supported on a floor surface 20 of the surgical environment 10. Alternatively or additionally, the base 110 is attached to a gantry above the floor surface 20 and mounted onto walls or ceilings of the surgical environment.

In some implementations, the surgical system 100 includes one or more of a surgeon's console 124, an electronics cart 126, a tray 128, an accessory table 130 or an anesthesia cart 132. In the example shown in FIG. 1, the patient 102 to be treated is positioned on an operating table 134. A surgeon 136 operates the surgeon's console 124 to control the remotely controllable arm 106 of the surgical manipulator assembly 104 during the surgery. An anesthesiologist or assistant 137 can administer anesthesia from the anesthesia cart 132 to the patient 102 during the surgery, and another assistant 139 can select surgical tools on the tray 128 to be mounted onto the surgical manipulator assembly 104.

To perform the surgery, the surgeon 136 can manipulate the remotely controllable arm 106 of the surgical manipulator assembly 104 by operating the console 124. The console 124 can be positioned within the surgical environment 10 or, in some cases, can be positioned at a remote location outside of the surgical environment 10. The console 124 enables the surgical system 100 to be used for minimally invasive telesurgery. The surgeon 136 operates the surgeon's console 124 to control the remotely controllable arm 106 of the surgical manipulator assembly 104 and manipulate the surgical tool mounted to the remotely controllable arm 106.

In some implementations, the surgeon's console 124 includes a display so that the surgeon 136 to view a surgical site through images captured by an imaging device. The display is, for example, a stereoscopic display that shows stereoscopic images of the surgical site. While viewing the images of the surgical site, the surgeon 136 can perform the surgical procedures on the patient 102 by manipulating control input devices on the surgeon's console 124, which in turn control motion of the remotely controllable arm 106 of the surgical manipulator assembly 104.

In some implementations, the control input devices of the surgeon's console 124 include manual input devices graspable by hands of the surgeon 136. Manipulation of the manual input devices, for example, causes the surgical manipulator assembly 104 to move the remotely controllable arm 106 on the surgical manipulator assembly 104. Degrees of freedom of the remotely controllable arm 106 are, for example, sufficient to enable the surgeon 136 to manipulate the manual input devices to translate and rotate the remotely controllable arm 106 to perform the surgery. The control input devices, alternatively or additionally, include foot pedals with either or both of toe and heel controls. The surgeon 136 can operate the foot pedals to cause movement or actuation of devices associated with the foot pedals. The surgeon 136 can depress a foot pedal to cause actuation of an end effector. The surgeon's console 124 includes a controller, e.g., a processor that generates signals in response to mechanical motion of the control input devices of the surgeon's console 124. The signals, for example, cause corresponding motion of the remotely controllable arm 106 of the surgical manipulator assembly 104.

In some implementations, the electronics cart 126 is connected with the imaging device that generates the images of the surgical site. The surgical manipulator assembly 104, for example, includes the imaging device connected to the electronics cart 126. The imaging device may include illumination equipment (e.g., a Xenon lamp) that provides illumination for imaging the surgical site. The imaging device can capture the images and then transmit the images to the electronics cart 126 for processing. The electronics cart 126 then can transmit the images to the surgeon's console 124 so that the processed images can be presented to the surgeon 136. The electronics cart 126 can include optional auxiliary surgical equipment, such as electrosurgical units, insufflators, suction irrigation instruments, or third-party cautery equipment.

Figure 2:
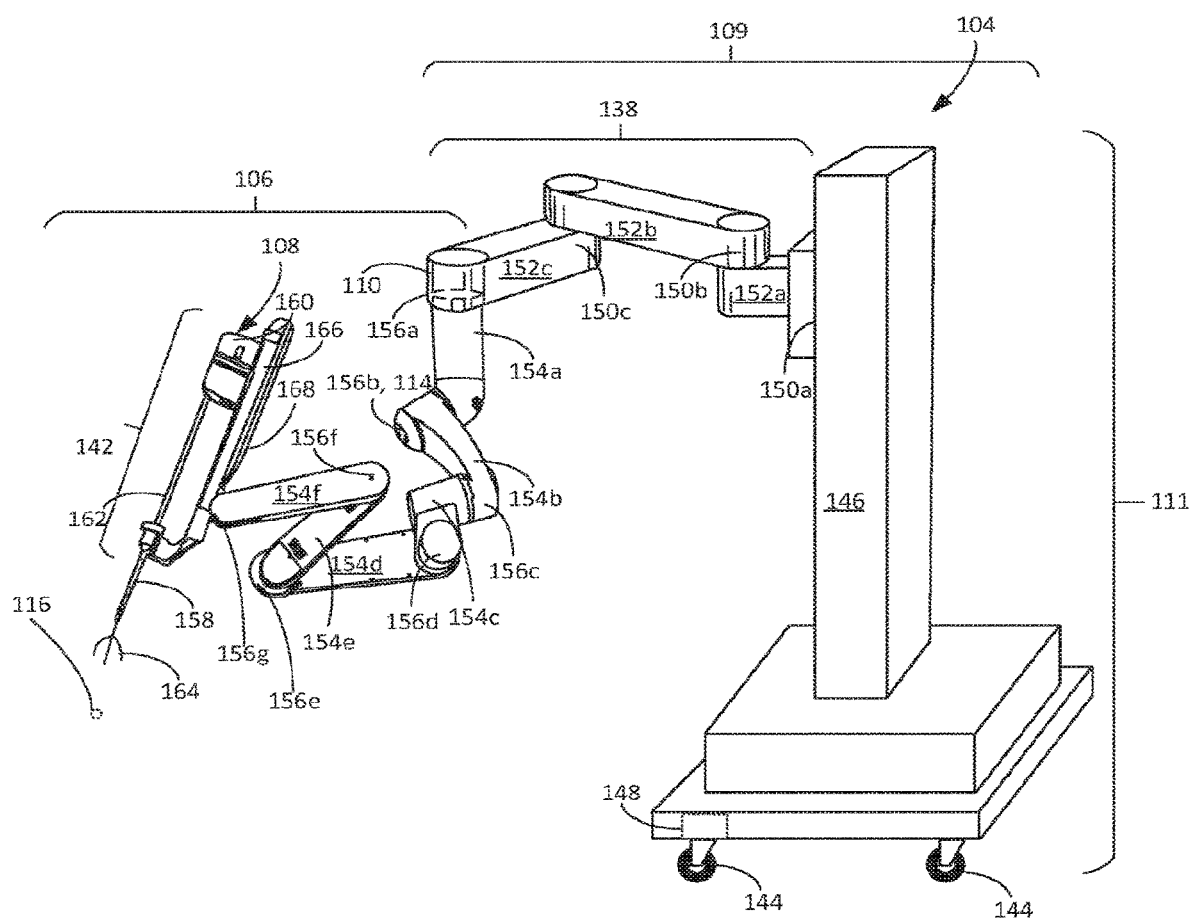
FIG. 2 is a perspective view of a manipulator assembly.

FIG. 2 depicts an example of a manipulator assembly that may be configured to operate as the surgical manipulator assembly 104. The remotely controllable arm 106 of the surgical manipulator assembly 104 extends from the base 110. The surgical manipulator assembly 104 includes an instrument holder 142 connected to the remotely controllable arm 106 and to which a surgical tool 108 is mounted. The base 110 is movably supported above the floor surface 20 of the surgical environment 10 such that a powered joint of the remotely controllable arm 106, when driven, can reposition the base 110 above the floor surface 20.

In some implementations, the surgical manipulator assembly 104 includes a setup assembly 109 that supports the base 110 above the floor surface The setup assembly 109 is, for example, supported on the floor surface 20 and supports the base 110 above the floor surface 20. In some cases, the setup assembly 109 is supported by walls or a celling of the surgical environment to support the base 110 of the above the floor surface 20. In some cases, as described herein, the setup assembly 109 is supported by the operating table 134.

In some implementations, as shown in the example of FIG. 2, the setup assembly 109 includes a setup arm 138 extending from a cart 111. The cart 111 is, for example, movable omnidirectionally across the floor surface 20. In some cases, the cart 111 includes wheels 144 so that the cart 111 is movable across the floor surface 20 through rolling motion of the wheels 144. The wheels 144 enable the surgical manipulator assembly 104 to be transported from location to location, such as between operating rooms or within an operating room to position the surgical manipulator assembly 104 near an operating table (e.g., the operating table 134 of FIG. 1). In some cases, a braking mechanism 148 is coupled to one or more of the wheels 144. In some cases, the operator manually manipulates the setup assembly 109 and/or the cart 111 to reposition the base 110.

The setup arm 138 includes, for example, a first setup joint 150a that connects the setup arm 138 to the column 146. In some cases, the setup arm 138 includes several links connected to one another by joints. The setup arm 138 includes, for instance, a first setup link 152a, a second setup link 152b, and a third setup link 152c. In some cases, the setup arm 138 further includes a second setup joint 150b, and a third setup joint 150c. The first joint 150a connects a proximal end of the first setup link 152a to the column 146. The second setup joint 150b connects a distal end of the first setup link 152a to a proximal end of the second setup link 152b. The third setup joint 150c connects a distal end of the second setup link 152b to a proximal end of the third setup link 152c. A distal end of the third setup link 152c is connected to the base 110. In some cases, the first joint 150a is a prismatic joint enabling the setup arm 138, and hence the remotely controllable arm 106, to be translated vertically above the floor surface 20 relative to the cart 111. In some cases, the second and third setup joints 150b-150c are revolute joints such that any two of the setup links 152a, 152b, 152c connected to one another by one of the joints 150b, 150c are rotatable relative to one another about the connecting joint.

In some implementations, the cart 111 includes a column 146 extending vertically upward when the cart 111 is supported on the floor surface 20. The setup arm 138 is, for example, connected to the column 146 of the cart 111. The first joint 150a, for instance, connects the setup arm 138 to the column 146 such that the setup arm 138 can be translated vertically along the column 146.

In some implementations, the remotely controllable arm 106 is connected to the distal portion of the setup arm 138. In some cases, the remotely controllable arm 106 includes a series of links and joints connected to the instrument holder 142. The remotely controllable arm 106 includes, for example, manipulator links 154a-154f connected to one another in series. A manipulator joint 156a connects the manipulator link 154a to the setup link 152c. The manipulator joints 156b-156f connect the manipulator links 154a-154f to one another such that the manipulator links 154a-154f can be moved relative to one another. A manipulator joint 154g of the remotely controllable arm 106 movably supports the instrument holder 142.

Alternatively or additionally, the manipulator joint 156a is a revolute joint enabling relative rotation of the remotely controllable arm 106 and the base 110. In some cases, the manipulator joints 156b-156f are each revolute joints that enable relative rotation between the manipulator links 154a-154f. In some cases, the instrument holder 142 is pivotably coupled to the manipulator link 154f of the remotely controllable arm 106 so that the instrument holder 142 is rotatable relative to the remotely controllable arm 106. In some cases, the manipulator joint 156g is a revolute joint that enables the instrument holder 142 to pivot at the manipulator joint 156g and to thereby rotate relative to the remotely controllable arm 106. In some examples, the joint 156g is a wrist joint enabling pivotal motion about two axes.

The instrument holder 142 is configured to hold the surgical tool 108. The instrument holder 142 is also, in some cases, configured to hold a cannula 158, which is a tubular member to be inserted into the access port 112 on the patient 102. The cannula 158 and the surgical tool 108 are releasably coupled to the instrument holder 142 so that different types of cannulas and surgical tools are mountable to the instrument holder 142.

In some implementations, the surgical tool 108 includes a transmission assembly 160 positioned at a proximal end of an elongate shaft 162. The transmission assembly 160 is actuated, for example, to cause motion of an end effector 164 positioned at a distal end of the elongate shaft 162. In some cases, the end effector 164 of the surgical tool 108 is controlled in a manner to manipulate tissue of the patient 102, treat tissue, image tissue, or perform other operations during the surgery. The cannula 158 defines a lumen to receive the elongate shaft 162 of the surgical tool 108 such that the elongate shaft 162 can be slidably disposed within the lumen of the cannula 158. The elongate shaft 162 defines a longitudinal axis coincident with a longitudinal axis of the cannula 158. The instrument holder 142 includes, for instance, an instrument holder carriage 166 translatable along an instrument holder frame 168 such that the elongate shaft 162 of the surgical tool 108 can be translated along its longitudinal axis. The elongate shaft 162 and the end effector 164 are insertable into and retracted from the lumen of the cannula 158 and the access port 112 on the patient 102 such that the end effector 164 can perform operations during the surgery.

The term "tool" encompasses both general or industrial robotic tools and specialized robotic medical instruments (including robotic surgical instruments and robotic medical instruments for diagnoses and non-surgical treatment). The tool/manipulator interface, e.g., the instrument holder 142, can be a quick disconnect tool holder or coupling, allowing rapid removal and replacement of the tool with an alternate tool. Although the specific examples presented in this disclosure are often surgical examples, the techniques disclosed are also applicable to non-surgical use. For example, they may be used with and improve general or industrial robotic operations, such as those use in manipulating work pieces. These techniques may also be used with and improve medical robotic operations for diagnoses and non-surgical treatment.

Further, although the specific examples presented in this disclosure often discuss teleoperational robotic systems, the techniques disclosed are also applicable to robotic systems that are directly and manually moved by operators, in part or in whole. For example, these techniques can be applied to robotic systems designed to help steady a tool held by the robotic arm while the tool is manipulated manually by an operator. As another example, any of the controllable arms discussed herein, including arms 106, 904A, 904B, 904C, 1004, 1100 may be configured to allow direct manipulation, and accept operator instruction through input directly applied to a link or a joint of the manipulator.

The setup assembly 109, the base 110, and the remotely controllable arm 106 form a kinematic chain to control the surgical tool 108 supported by the remotely controllable arm 106, e.g., supported by the instrument holder 142 of the remotely controllable arm 106. For example, a proximal end of the setup assembly 109 is supported on the floor surface 20, a distal end of the setup assembly 109 is connected to the base 110, the base 110 is connected to a proximal end of the remotely controllable arm 106, and a distal portion 159 of the remotely controllable arm 106 is configured to hold a cannula 158. The setup assembly 109, the base 110, the remotely controllable arm 106 are kinematically connected in series. As a result, movement of one or more joints of the surgical manipulator assembly 104, movement of the cart 111, or movement of both the surgical manipulator assembly 104 and the cart 111 can cause motion of the distal portion 159 (or the cannula 150 or the surgical tool 108 if present and held by the instrument holder 142) relative to the floor surface. A portion of the surgical tool 108 extends through cannula 158 when the surgical tool 108 is mounted to the remotely controllable arm 106. When the surgical tool 108 is mounted to the remotely controllable arm 106, the setup assembly 109, the base 110, the remotely controllable arm 106, and the surgical tool 108 are kinematically connected in series. In this regard, in some cases, movement of a joint of the surgical manipulator assembly 104 or the cart 111 causes relative motion between the surgical tool 108 and the floor surface 20.

In some implementations, during the surgical operation, the base 110 is fixed above the floor surface. The setup assembly 109, for example, is fixed above the floor surface 20, thereby causing the base 110 to be stationary within the surgical environment 10 above the floor surface 20. Joints of the remotely controllable arm 106 are, for example, manipulated while the setup assembly 109 is fixed to cause motion of the surgical tool 108 to perform the surgery.

The surgical manipulator assembly 104 includes a number of degrees of freedom between the setup assembly 109 and the surgical tool 108 such that the surgical tool 108 can be placed in a range of possible positions, during the surgical operation. When the position of the base 110 is fixed within the surgical environment 10, movement of a joint of the surgical manipulator assembly 104 kinematically between the setup assembly 109 and the surgical tool 108 can cause motion of the surgical tool 108 relative to the floor surface 20. Actuation of the end effector 164 (such as opening or closing of the jaws of a gripping device, energizing an electrosurgical paddle, or the like) can be separate from, and in addition to, the manipulator assembly degrees of freedom.

In some examples, when the surgical tool 108 is fixed within the surgical environment 10 such that the surgical tool 108 does not move relative to the reference (such as a reference including reference point 116), movement of a joint of the surgical manipulator assembly 104 may exert a torque insufficient to cause substantial movement of the surgical tool 108. If the base 110 is allowed to move within the surgical environment in this case, the movement of the joint can cause a corresponding movement of the base 110 instead of movement of the surgical tool 108. As described herein, the powered joint 114 is controllable to backdrive the base 110 when the surgical tool 108 is fixed within the surgical environment 10, e.g., fixed relative the floor surface 20.

The joints of the remotely controllable arm 106 can have sufficient degrees of freedom to move the surgical tool 108 to the access port 112 of the patient 102 and within the access port 112 of the patient 102 to perform the surgery. The specific combination of joints described with respect to FIG. 2 is one example of the possible joint and link combinations and the degrees of freedom possible for the remotely controllable arm 106. The revolute joints, which include the joints 150b-150c, 156a-156g, each connect two links to enable the links to rotate relative to one another about a joint axis defined by the revolute joint. The prismatic joints, which include the joint 150a as well as the joint between the instrument holder frame 168 and the instrument holder carriage 166, allow for translation along a joint axis defined by the prismatic joint.

In some implementations, one or more of the joints 150a-150c, 156a-156g of the surgical manipulator assembly 104 are powered joints. These powered joints are, for example, actuated to cause relative motion of connecting links. The powered joints are, for example, controlled by the surgeon 136 using control inputs on the surgeon's console 124. The surgeon 136, upon manipulating the control inputs on the surgeon's console 124, causes a command to be transmitted to an actuator of a powered joint. The command, for example, activate the actuator of the powered joint, in turn causing two or more links connected by the powered joint to move relative to one another. The joint 156g movably supporting instrument holder 142 is, for example, a powered joint that enables the surgeon 136 to cause the surgical tool 108 to move when the powered joint is actuated.

In some implementations, one or more of the joints 150a-150c, 156a-156g are passive joints that are not actively controlled by a processor or processors of the surgical system 100. A passive joint, instead of being actively controlled, is movable in response to movement of actively controlled joints. In some examples, the passive joints of the remotely controllable arm 106 can be selectively releasable. A passive joint can include a release mechanism that enables motion of the passive joint when activated. For example, the release mechanism can include a releasable clamp that, when operated, causes the passive joint to be released and to be movable. A passive joint can include a braking mechanism that, upon release, allows motion of the joint or, upon actuation, inhibits motion of the joint. In some implementations, the surgeon 136 or other operator manually interacts with the joints of the surgical manipulator assembly 104 to cause movement of the joints.

The remotely controllable arm 106 can have more degrees of freedom than necessary to place the distal portion of the arm 106 (or the surgical tool 108 or other device mounted on arm 106, if present) in a given position, e.g., the arm 106 can have redundant degrees of freedom. For example, in some implementations, the remotely controllable arm 106, the setup arm 138, or the remotely controllable arm 106 and the setup arm 138 together include a plurality of joints that provide sufficient degrees of freedom to allow a range of joint states for (1) a pose of the base 110 and (2) a state of a distal portion of the remotely controllable arm 106 or of an end effector of the surgical tool 108.

The manipulator linkages can have sufficient degrees of freedom so as to occupy a range of joint states for a given state of the distal portion of the arm 106 (or the surgical tool 108 or other device mounted on arm 106, if present). Such structures may include linkages having redundant degrees of freedom. In these structures, in some implementations, actuation of one joint may be directly replaced by a similar actuation of a different joint along the kinematic chain. These structures are, in some cases, referred to as having excess, extra, or redundant degrees of freedom. These terms can encompass kinematic chains in which, for example, intermediate links move without changing the pose of an end effector.

"Linkage" is used in this application to indicate a structure including a single link, at least one link, or multiple links as applicable given the context. In these structures, in some implementations, actuation of one joint may be directly replaced by a similar actuation of a different joint along the kinematic chain. These structures are, in some cases, referred to as having excess, extra, or redundant degrees of freedom. These terms can encompass kinematic chains in which, for example, intermediate links can move without changing the pose of an end effector.

In this regard, in a given position of the distal portion of the arm 106 (or of the surgical tool 108 or other device mounted on the arm 106, if present), each joint of the remotely controllable arm 106 can occupy or be driven to a joint state within a range of available joint states. Each link of the remotely controllable arm 106 can occupy or be driven within a range of alternative linkage positions. In the given position of the distal portion of the arm 106 (or of the surgical tool 108 or other device mounted on the arm 106, if present), each joint of the remotely controllable arm 106 can have a range of joint velocity vectors or speeds. The ranges of available joint states, the ranges of alternative linkage positions, and the ranges joint velocity vectors or speeds can be defined by the number and types of degrees of freedoms.

The term "state" of a joint can refer to control variables associated with the joint. For example, the state of a revolute joint that enables relative rotation between links can include an angle defined by the joint within a range of motion and/or an angular velocity of the joint. The state of a prismatic joint may refer to an axial position and/or an axial velocity of the joint.

Movement of the setup arm 138 and the remotely controllable arm 106 may be controlled by a processor so that the surgical tool 108 is constrained to a desired motion through the access port 112. Such motion can include, for example, axial insertion of the elongate shaft 162 through the access port 112, rotation of the elongate shaft 162 about its longitudinal axis, and pivotal motion of the elongate shaft about a pivot point adjacent the access port 112.

In some examples, these motions may be inhibited through use of robotic data processing and control techniques of the joints of the remotely controllable arm 106. The joints 156a-156g of the remotely controllable arm 106 can be controlled to maintain a position and/or orientation of the distal portion of the arm 106 (or of a cannula or surgical tool 108 or other item mounted to the arm 106) relative to a reference (such as a reference including the reference point 116) in the surgical environment 10. In some examples, only one of the joints of the remotely controllable arm 106 is controlled to maintain a position and/or orientation of the distal portion of the arm 106 (or of a cannula or surgical tool 108 or other item mounted to the arm 106) relative to a reference (such as the reference point 116) in the surgical environment 10. In some examples, multiple joints of the remotely controllable arm 106 are controlled to maintain the position and/or orientation. Where the orientation of the distal portion 159 (or cannula 158 or surgical tool 108 if present) is maintained as well, the reference may include a reference frame with an origin at reference point 116.

The reference point 116 can coincide with a remote center of motion constraining motion of the distal portion of the arm 106 (or of a cannula or surgical tool 108 or other item mounted to the arm 106). In particular, the reference point 116 may also be a pivot point about which the distal portion of the arm 106 (or of a cannula or surgical tool 108 or other item mounted to the arm 106) rotates. In some cases, the reference point 116 may coincide with the access port 112 on the patient 102 such that, as the surgical tool 108 is moved, the point at which the surgical tool 108 enters into the anatomy of the patient 102 through the access port 112 does not move relative to the reference point 116, thereby reducing stresses on the anatomy of the patient 102 at the reference point 116. The joints 156a-156g can be controlled such that any point along the surgical tool 108 is rotated about the reference point 116 when the joints 156a-156g are moved. The joints 156a-156g can have sufficient available degrees of freedom such that, when a first set of joints is moved, in response, a second set of joints can be moved to maintain the position and/or orientation of the distal portion of the arm 106 (or of a cannula or surgical tool 108 or other item mounted to the arm 106). In this regard, joints 156a-156g can be moved toward optimum poses within the surgical environment 10 without causing movement of the surgical tool 108. In some implementations, the joints 156a-156g, or a subset of the joints 156a-156g, have multiple configurations that maintain a particular position and/or orientation of the distal portion of the arm 106 (or of a cannula or surgical tool 108 or other item mounted to the arm 106).

Other examples of software-constrained remote centers of motion of robotic arms and manipulators are described in U.S. Pat. No. 8,004,229 (herein referred to as "the '229 Patent") published on Aug. 23, 2011, the entirety of which is hereby incorporated by reference in its entirety.

Figure 3:
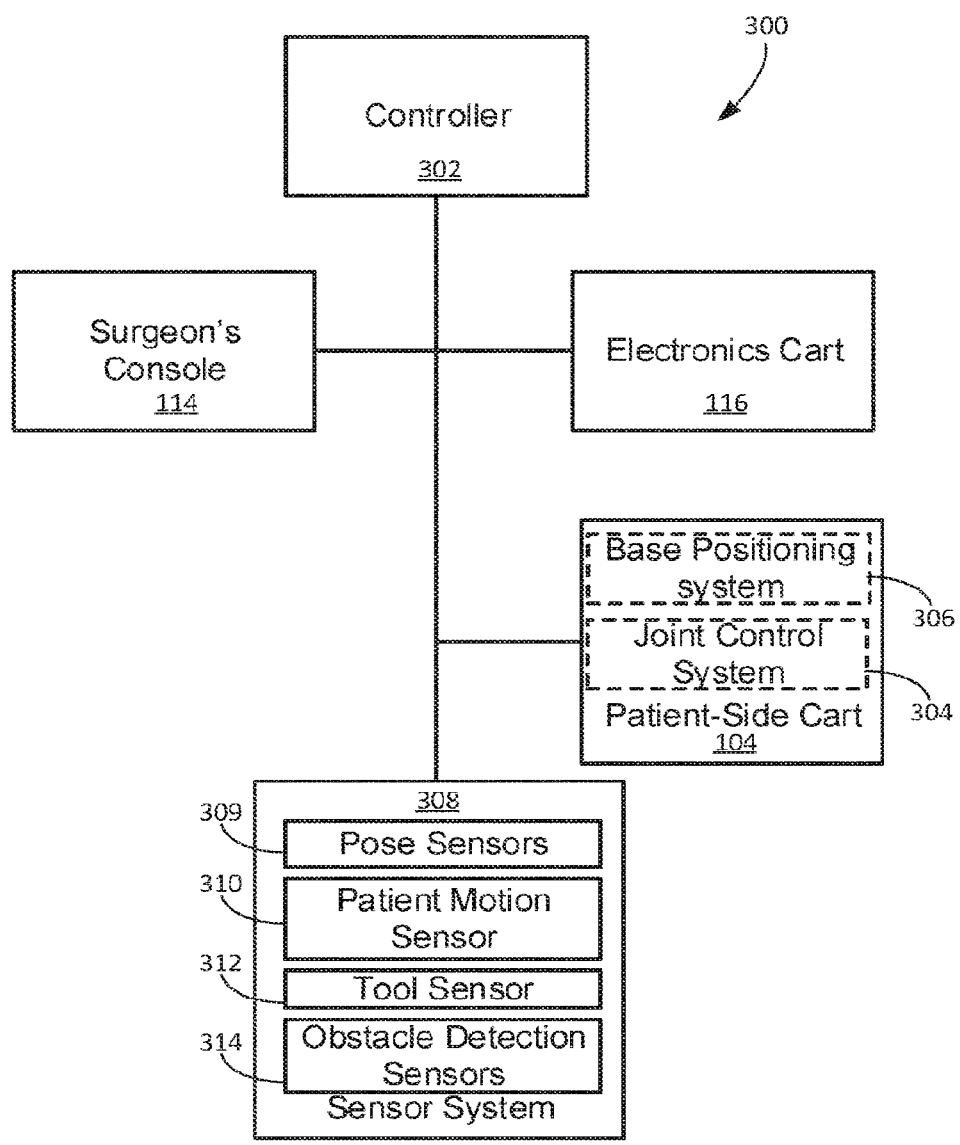
FIG. 3 is a block diagram of a control system for the surgical system of FIG. 1.

Referring also to FIG. 3, a surgical system 100 can include a control system 300 that can control operations of the equipment of the surgical system 100. During surgery, the control system 300 can control the surgical manipulator assembly 104, e.g., joints of the remotely controllable arm 106 of the surgical manipulator assembly 104, to maintain the position and/or orientation of the surgical tool 108 using a software-constrained remote center approach described in the '229 Patent. The control system 300 includes a processor 302 and the surgical manipulator assembly 104. The surgical manipulator assembly 104 includes a joint control mechanism 304 and a base positioning system 306. The control system 300 includes, in some implementations, one or more of the surgeon's console 124, the electronics cart 126, and a sensor system 308.

The processor 302 can be one of several processors. Each of the surgeon's console 124, the surgical manipulator assembly 104, the electronics cart 126, the joint control mechanism 304, and the base positioning system 306 of the control system 300 can include independent processors for controlling operations. A wired or wireless connection can enable communication between the surgical manipulator assembly 104, the electronics cart 126, the surgeon's console 124, and the base positioning system 306. The connection can be, for example, an optical fiber communication link between the surgeon's console 124, the electronics cart 126, and the surgical manipulator assembly 104. The control system 300, in some examples, can include a single processor that serves as a central electronic data processing unit capable of performing some or all of the data processing used to operate the surgical system 100.

The joint control mechanism 304 can be operated to manipulate the surgical tool to perform a surgical procedure. The joint control mechanism 304 can selectively actuate powered joints of the remotely controllable arm 106, selectively release selectively releasable passive joints of the remotely controllable arm 106, and selectively control braking mechanisms associated with the joints of the remotely controllable arm 106. When the surgeon 136 operates the surgeon's console 124 to direct the surgery, the processor 302 can receive input signals from the surgeon's console 124. The processor 302 then generates corresponding control signals for the joint control mechanism 304 to manipulate the joints, thereby moving the surgical tool 108 to perform the surgery on the patient 102.

During surgery, the processor 302 can determine or estimate a remote center of motion for the surgical tool 108 and can control actuation of a powered joint, e.g., the powered joint 114, of the remotely controllable arm 106 to maintain the remote center of motion for the surgical tool 108. The processor 302 optionally uses inverse kinematics to determine how the joints should be driven to maintain the position and/or orientation of the surgical tool 108. The actuator of the powered joint can be selectively driven to maintain the position and/or orientation of the surgical tool 108 and/or to position the powered joint in a more optimal position. In some cases, the processor 302 controls the actuator of the powered joint to inhibit motion of the powered joint that may result due to the movement of the base 110. In some examples, the processor 302 controls the actuator of the powered joint to cause motion of the powered joint toward a more optimal position.

The processor 302 can constrain the motion of the surgical tool 108 such that the surgical tool 108 rotates about a pivot point, e.g., corresponding to the location of the access port 112. In estimating the pivot point, the processor 302 can selectively implement different modes characterized by a compliance or stiffness of the remotely controllable arm 106. The processor 302 can implement different modes over a range of compliance or stiffness for the pivot point or remote center of motion after an estimate pivot point is computed. The range can span between a pivot point being compliant, e.g., resulting in a passive pivot point, and a pivot point being stiff, e.g., resulting in a fixed pivot point.

For a fixed pivot point, the estimated pivot point can be compared to a desired pivot point to generate an error output that can be used to drive the pivot point of the surgical tool 108 to the desired location. For a passive pivot point, the desired pivot location may not be a primary or overriding objective. The estimated pivot point can still be used for error detection. Changes in estimated pivot point locations may indicate that the patient 102 has been moved or that a sensor is malfunctioning, thereby giving the processor 302 an opportunity to take corrective action.

The processor 302 optionally allows the compliance or stiffness of the remotely controllable arm 106 to be changed throughout the range. For example, the joint 156g can be an instrument holder wrist joint enabling pivotal motion about two axes. When the joint 156g is controlled to be at the compliant end of the range, the processor 302 can move the proximal end of the surgical tool 108 in space while the actuators of the joint 156g apply little or no torque. In this regard, the surgical tool 108 acts effectively like it is coupled to the remotely controllable arm 106 by a pair of passive joints. In this mode, the interaction between the elongate shaft 162 and the tissue of the patient 102 along the access port induces the pivotal motion of the surgical tool 108 about the pivot point. If the surgical tool 108 was not inserted into the minimally invasive aperture or otherwise constrained, it may point downward under the influence of gravity, and movement of the remotely controllable arm 106 would translate the surgical tool 108 without pivotal motion about a point along the elongate shaft 162.

When the joint 156g is controlled to be at the stiff end of the range, the processor 302 may determine the location of the access port from the port data 514 and use the location of the access port as the pivot. The processor 302 thus may control the joints of the remotely controllable arm 106 such that the remotely controllable arm 106 behaves in a manner similar to mechanically constrained remote center linkages. Implementations may fall between providing calculated motion about a pivot point corresponding to the access site and moving the remote center of motion within an acceptable range when the tissue along the access port moves without imposing excessive lateral forces on the tissue. The '229 Patent—the entirety of which is incorporated herein by reference in its entirety—describes other examples of computing remote centers of motion and pivot points.

During the surgery, the joint control mechanism 304 can control one or more powered joints of the remotely controllable arm 106 in response to the control signals from the processor 302. The base positioning system 306 maintains the position and/or orientation of the base 110 relative to the floor surface 20 of the surgical environment 10 such that torque applied by the powered joint is transmitted to the instrument holder 142 to move the surgical tool 108.

In some implementations, the base positioning system 306 controls the position of the base 110 by locking the base 110 during the surgery. The base positioning system 306 includes, for example, brakes or locks associated with the cart 111 or the wheels 144 of the cart 111 that, when activated, inhibit the cart 111 from moving about the surgical environment 10. While the base positioning system 306 maintains the position and/or orientation of the cart 111, the joint control mechanism 304 actuates the powered joint to cause motion of the links of the remotely controllable arm 106, and thus cause motion of the surgical tool 108. The motion of the surgical tool 108 enables the surgery to be performed.

In some implementations, the base positioning system 306 is operated to inhibit or enable movement of the base 110 relative to the floor surface 20. In particular, the base positioning system 306 can release the locks or brakes associated with, for example, joints kinematically positioned between the base 110 and the powered joint 114. When the joints are released, the base positioning system 306 operates the joint control mechanism 304 in such a manner that the base 110 is moved about the surgical environment 10. The base positioning system 306 can control the powered joint or powered joints of the remotely controllable arm 106 of the surgical manipulator assembly 104 to backdrive the base 110 of the surgical manipulator assembly 104 to a desired pose within the surgical environment 10. When the base 110 is free to move within the surgical environment 10 and the distal portion of the arm 106 (or of a cannula or surgical tool 108 or other item mounted to the arm 106) is kept fixed relative to a reference (such as a reference including the reference point 116) within the surgical environment 10, actuation of the powered joint 114 backdrives the base 110. The process of backdriving the base 110 can be used to move the base 110 toward the optimal base location envelope 122.

In some cases, the base positioning system 306 can operate the joint control mechanism 304 to control active and/or passive joints of the surgical manipulator assembly 104 in addition to the powered joint. The base positioning system 306 can also be controlled to position joints of the remotely controllable arm 106 toward optimal positions or optimal ranges of positions. In the example depicted in FIGS. 1 and 2, the joint 156b of the remotely controllable arm 106 corresponds to the powered joint 114, and the joint control mechanism 304 controls the powered joint 114 to position the base 110. For example, the reference includes a reference point 116 that coincides with the access port 112. The tissue of the patient 102 can provide sufficient reaction force to prevent motion of the distal portion of the arm 106 (or of a cannula or surgical tool 108 or other item mounted to the arm 106) when the powered joint 114 is driven. When the powered joint 114 is driven, the tissue of the patient 102 can inhibit motion of the surgical tool 108. While the position and/or orientation of the distal portion of the arm 106 (or of a cannula or surgical tool 108 or other item mounted to the arm 106) is externally maintained, the base 110 is able to move about the surgical environment 10. The base positioning system 306 therefore can control the joint control mechanism 304 to drive the powered joint 114 to backdrive the base 110 and thereby move the base toward the optimal base location envelope 122. The torque from the powered joint 114, instead of causing motion of the distal portion of the arm 106 (or of a cannula or surgical tool 108 or other item mounted to the arm 106), can cause motion of the base 110. In this regard, the powered joint 114, which can be used during surgery to control motion of the surgical tool 108 to perform dexterous surgical maneuvers, can also be driven to backdrive the base 110.

In some cases, when the joint control mechanism 304 operates the powered joint 114 to position the base 110, the joint control mechanism 304 can also control operations of the other joints of the remotely controllable arm 106. If the joints 150a-150c are selectively releasable joints, the joint control mechanism 304 can selectively lock these joints when the powered joint 114 is driven to backdrive the base 110. For example, the joint control mechanism 304 can lock each of these joints such that a substantial portion of the torque from actuation of the powered joint 114 is transmitted through the joints to the base 110.

The powered joint 114 alternatively or additional can backdrive any joints positioned between the base 110 and the powered joint 114. For example, if the joints 150a-150c are passive joints, the powered joint 114 can be driven to backdrive each of the joints 150a-150c. The joint control mechanism 304 can release the selectively releasable passive joints of the remotely controllable arm 106 such that, when the powered joint 114 is driven, the joints 150a-150c are backdriven. The processor 302 can selectively release and lock the passive joints as well as the base 110 such that each of the passive joints and the base 110 are moved indirectly toward their optimal positions or optimal ranges of positions. The repositioning of the passive joints through backdriving the passive joints can occur while the position and/or orientation of the surgical tool 108 is maintained using the methods described herein.

The base positioning system 306 optionally controls operations of the braking mechanism and/or a drive mechanism associated with the base 110, for example, associated with the wheels 144 of the base 110. If the joints 150a-150c are selectively releasable joints and the joint control mechanism 304 is used to reposition these joints, the base positioning system 306 can lock the base 110 while driving the powered joint 114 and while one or more of the joints 150a-150c are released. The joint control mechanism 304 can drive the powered joint 114 to reposition the selectively releasable joints while the position and/or orientation of the base 110 is maintained.

To position a passive joint, the base positioning system 306 can lock the base 110 and each of the other passive joints. The base positioning system 306 can then actuate the powered joint to backdrive the joint toward its optimum position. The base positioning system 306 can repeat this process for each of the joints and for the base. The powered joint 114 can thus be driven to move the joints 150a-150c and the base 110 toward optimal positions.

If the wheels 144 are powered wheels, the processor 302 can control the base positioning system 306 to facilitate or inhibit repositioning. For example, the processor 302 can control the orientation of wheels 144 such that the wheels 144 are aimed to roll along a repositioning direction or not to roll along a non-repositioning direction. Thus, the processor 302 can control the wheels 144 to move the base 110 by activating the powered wheels to drive, for example, the cart 111. The movement of the cart 111 then causes the base 110 to move toward a position adjacent the patient 102. After the surgical tool 108 is secured and the powered wheels have been driven to move the base 110 toward the position adjacent the patient, the processor 302 can then control the base positioning system 306 to deactivate the powered wheels and operate the powered joint 114 to backdrive the base 110 toward the optimal base location envelope 122.

In some examples, the processor 302 can control the base positioning system 306 to activate the powered wheels in response to the displacement of the handle associated with the base 110 due to the operator pushing or pulling the handle. The processor 302 can activate the actuators driving the powered wheels to assist the operator to manually move the base 110. Instead of pushing or pulling the handle, the operator can alternatively grasp the distal portion of the remotely controllable arm 106. The operator can actuate an input button on the distal portion of the remotely controllable arm 106 to indicate that the operator intends to manually reposition the base 110. The base positioning system 306 can then drive the powered wheels to assist the operator to manually move the base 110. The base positioning system 306 can also operate the joints of the remotely controllable arm 106 so that the force applied by the operator is transmitted to the base 110. The joint control mechanism 304 can lock or brake each of the joints of the remotely controllable arm 106 to facilitate the force transfer. In some examples, to detect that the operator has grasped the distal portion of the remotely controllable arm 106 and is intending to pull the distal portion of the remotely controllable arm 106 to reposition the base 110, torque or force sensors of the remotely controllable arm 106 can detect the force applied by the operator. The processor 302 can receive signals from these sensors and proceed to drive the powered wheels and lock the joints of the remotely controllable arm 106 to assist the operator with manually repositioning the base 110.

The surgical system 100 can include sensors part of the sensor system 308 to detect treatment parameters and conditions of equipment in the surgical system. The surgical manipulator assembly 104 can include pose sensors 309 positioned at, for example, the joints 150b-150c and 156a-156g to detect relative poses of links along the surgical manipulator assembly 104. The pose sensors 309 can include a combination of pressure sensors, torque sensors, force sensors, position sensors, velocity sensors, accelerometers, rotary encoders, linear encoders, and other appropriate sensors to determine position and orientation of links and joints in the surgical manipulator assembly 104.

The pose sensors 309 can generate signals indicative of relative positions and orientations of the base 110, the setup assembly 109, and one or more of the joints 150a-150c and 156a-156g. In some cases, these pose sensors 309 detect a pose of the remotely controllable arm 106 relative to a pose of the base 110, detect a pose of one link relative to another link, detect a pose of the surgical tool 108 relative to the base 110, or poses of other elements of the surgical manipulator assembly 104 (such as the pose of a distal portion of the arm 106, or of a cannula or other item mounted to the arm 106). For a given joint with a pose sensor, the pose sensor can detect a joint state of the joint. The sensor can detect the position and velocity of the joint within the available range of joint states and joint velocities for a given position of the distal portion of the arm 106 (or of a cannula or surgical tool 108 or other item mounted to the arm 106). The sensor can also detect relative link poses of the links connected at the given joint. This sensor can thereby detect the pose of the link within the range of link states available at the given pose of the distal portion of the arm 106 (or of a cannula or surgical tool 108 or other item mounted to the arm 106).

In some implementations, the pose sensors 309 include a sensor that can detect a pose of the base 110 within the surgical environment 10. The sensor, for example, generates signals that can be used by the processor 302 to compute the pose of the base 110 based on movement of the setup assembly 109 supporting the base 110 and enabling the base 110 to be moved about the surgical environment 10. In some implementations, if the setup assembly 109 is supported within the surgical environment above the floor surface 20 on the wheels 144, the wheels 144 may be operable with rotary encoders that can be used to track the position and orientation of the cart 111 on the floor surface 20 of the surgical environment 10. The horizontal position and orientation of the base 110 can then be determined from the horizontal position and orientation of the cart 111. The cart 111 of the setup assembly 109 alternatively or additionally includes an optical sensor that can track motion, e.g., position, velocity, orientation, and/or acceleration, of the cart 111 along the floor surface 20. The optical sensor, for example, is similar to that used in an optical mouse. The optical sensor captures images of the floor surface 20 as the cart 111 moves relative to the floor surface 20. The images of the floor surface 20 vary with the movement of the cart 111. The processor 302, using the captured images, can determine a position and orientation of the cart 111.

In some examples, the pose sensors 309 include a sensor associated with a powered joint that can detect an external force that would cause articulation of the powered joint. In some cases, the powered joints are manually positionable by an operator. In response to the detection of the external force, the processor 302 of the control system 300 can actuate the actuator associated with the powered joint such that the powered joint moves in the direction of the external force. The processor 302 may counteract external forces below an appropriate threshold for the sensor, but may treat external articulations exceeding the threshold as an input into the remotely controllable arm 106.

In some examples, the processor 302 can determine the position of the distal portion of the arm 106 (or of a cannula or surgical tool 108 or other item mounted to the arm 106) directly by sensing motion of distal portion of the arm 106 (or of a cannula or surgical tool 108 or other item mounted to the arm 106). In some examples, the processor 302 can use forward kinematics to compute the motion of the distal portion of the arm 106 (or of a cannula or surgical tool 108 or other item mounted to the arm 106). Using actual joint motion information from the pose sensors 309, e.g., data indicative of the joint states of the joints of the controllable arm 106, the processor 302 can determine a pose of the distal portion of the arm 106 (or of a cannula or surgical tool 108 or other item mounted to the arm 106). Joint torques, forces, velocities, orientations, and/or positions optionally are transmitted to the processor 302 such that the processor 302 can determine the motion of the distal portion of the arm 106 (or of a cannula or surgical tool 108 or other item mounted to the arm 106). Using forward kinematics, the processor 302 can use the information from the pose sensors 309 to compute the pose of the distal portion of the arm 106 (or of a cannula or surgical tool 108 or other item mounted to the arm 106) relative to the base 110. In some examples, if the remote center of motion and the reference point 116 correspond to a position along the surgical tool 108, particularly, the point along the surgical tool 108 in which the surgical tool 108 is inserted into the access port on the patient 102, the processor 302 can determine the location of the reference point 116 and the remote center of motion based on the information from the pose sensors 309.

In some implementations, the sensor system 308 includes a patient motion sensor 310 to measure motion of the patient 102 relative to the distal portion of the arm 106 (or of a cannula or surgical tool 108 or other item mounted to the arm 106). The patient motion sensor 310 can include a sensor proximate to the distal portion of the arm 106 (or of a cannula or surgical tool 108 or other item mounted to the arm 106) that detects when a body of the patient 102 moves relative to the sensor. The sensor is, for example, an emitter-receiver sensor that detects a distance of nearby objects. The sensor can be an optical time-of-flight sensor that emits infrared light and receives the reflected infrared light to determine the distance of the patient 102. Relative changes in the distance over time can be indicative of patient motion.

The sensor system 308 alternatively or additionally includes a tool sensor 312 positioned such that the tool sensor 312 generates a sensor signal indicative of the force applied by the distal portion of the arm 106 (or of a cannula or surgical tool 108 or other item mounted to the arm 106) on the patient 102. The tool sensor 312 can be positioned on the surgical tool 108, the cannula 158, or another device in contact with the patient 102 to directly measure the applied force. In some examples, the tool sensor 312 is positioned at a joint, e.g., the joint 156g, to measure a torque. The processor 302 can then compute the applied force based on the torque at the joint 156g.

In some implementations, the sensor system 308 can include obstacle detection sensors 314. The obstacle detection sensors 314 can be positioned at one or more locations in the surgical system 100 to detect imminent collision or contact with nearby obstacles in the surgical environment 10. The surgical manipulator assembly 104 and/or the remotely controllable arm 106 can include obstacle detection sensors 314 to detect when the remotely controllable arm 106 contact or nearly contact nearby obstacles. The obstacles can include other equipment of the surgical system 100, such as the operating table 134, the electronics cart 126, and the surgeon's console 124. The obstacles can also include operators within the surgical environment 10, such as the surgeon 136, and the assistants 137, 139. The obstacle detection sensors 314 can include contact sensors, proximity sensors, optical time-of-flight sensors, and other sensors appropriate for detecting contact with an obstacle or a distance of an obstacle. The obstacle detection sensors 314 can also include, for example, tape switches, flexible sensing arrays, individual force sensing resistors or force sensing resistor arrays, or passive capacitive sensing systems. Signals from the obstacle detection sensors 314 can be monitored by the processor 302 of the control system 300, and, in some cases, the processor 302 may issue an alert upon determining that contact or collision may be imminent.

Example System Operation

As described herein, the control system 300 for the surgical system 100 can be used to reposition the base 110 of the remotely controllable arm 106 by operating the powered joint 114 to backdrive the base 110. For example, before the surgery is performed, the processor 302 can control the base positioning system 306 to reposition the base 110 toward the optimal base location envelope 122 adjacent the operating table 134. The base positioning system 306 can control the joint control mechanism 304 to operate the powered joint 114 to move the base 110.

Figure 4:
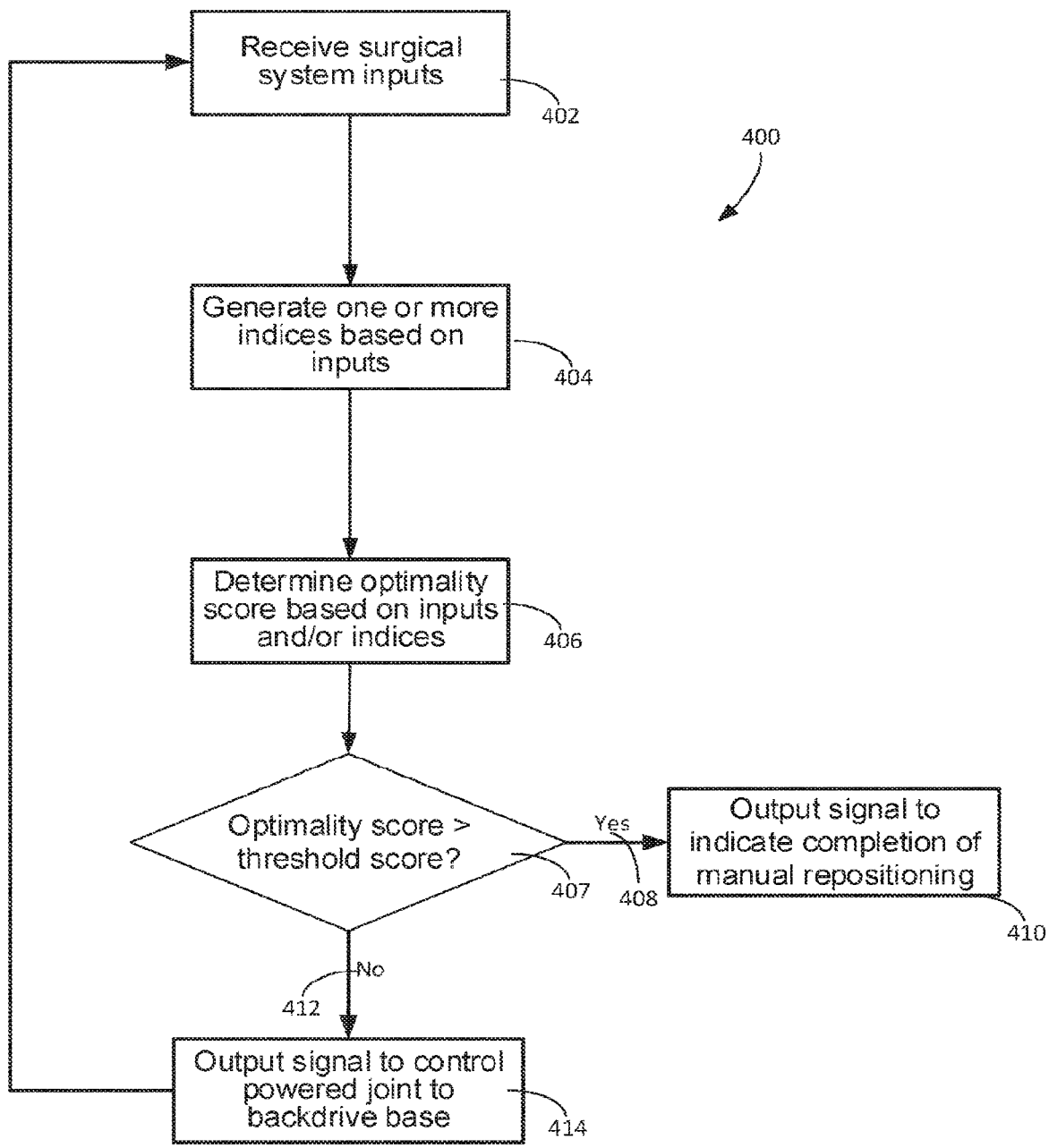
FIG. 4 is a flow chart of a process for backdriving with a powered joint to position a base.
Figure 5:
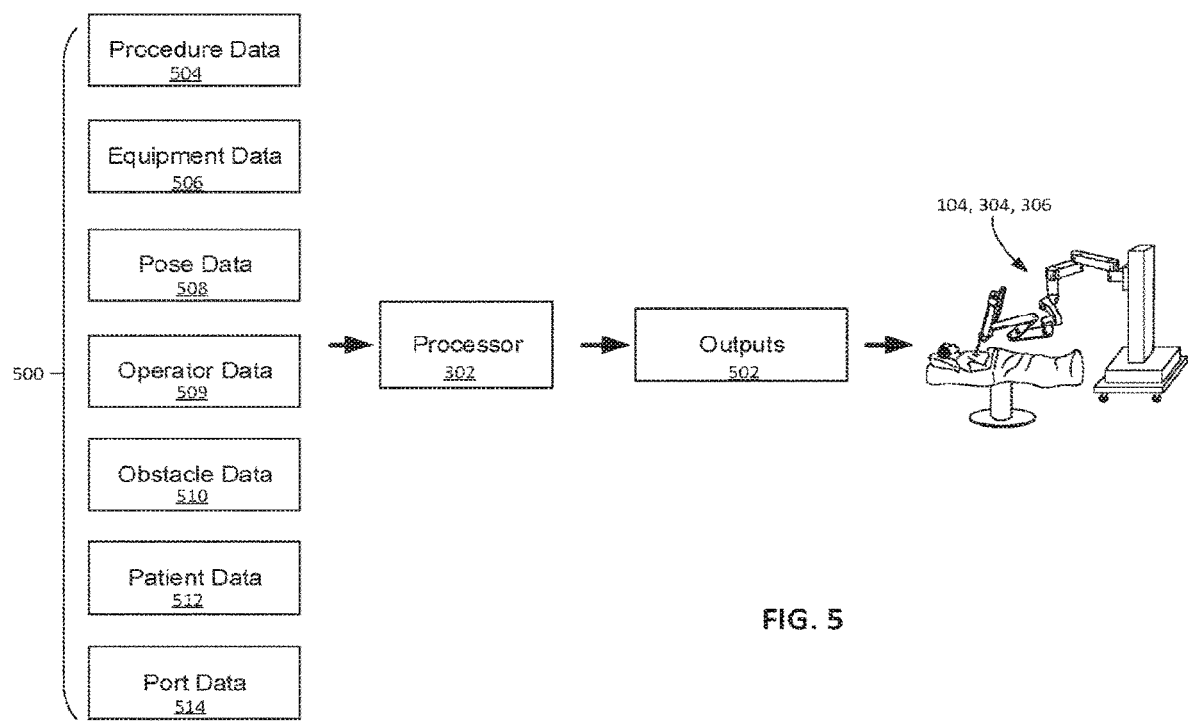
FIG. 5 is a diagram depicting inputs and outputs for a processor performing the process of FIG. 4.

When the powered joint 114 is actuated to move the base 110, the position and/or orientation of the surgical tool 108 relative to the reference (such as a reference including a reference point 116) is maintained. Example processes and operations to drive the powered joint 114 to position the base 110 while maintaining the position and/or orientation of the distal portion of the arm 106 (or of a cannula or surgical tool 108 or other item mounted to the arm 106) are described herein. FIG. 4, for instance, depicts a flow chart of a process 400 performed by the processor 302 to control the powered joint 114 to backdrive the base 110. FIG. 5 schematically depicts inputs and outputs used by the processor 302 to determine the signals outputted to control the powered joint 114. Although the process 400 is described with respect to the surgical system 100 of FIG. 1, the process 400 is applicable to other implementations of surgical systems described herein.

At the start of the process 400, the processor 302 receives (402) inputs from the surgical system 100. As shown in FIG. 5, the processor 302 can receive (402) inputs 500 from the surgical system 100, which the processor 302 processes to determine outputs 502 to control the base positioning system 306. The outputs 502 can include output signals to control the surgical manipulator assembly 104, e.g., the powered joint 114 of the surgical manipulator assembly 104, to backdrive the base 110. The inputs 500 can include user inputs specified by the operators as well as sensor signals generated by sensors of the sensor system 308. The inputs 500 can include, for example, procedure data 504, equipment data 506, pose data 508, operator data 509, obstacle data 510, patient data 512, and port data 514. The data 504, 506, 508, 510, 512, 514 represent some examples of the data usable by the processor 302 to control the processor 302 to control the base positioning system 306. Other types and contents of data may be appropriately used by the processor 302 to control the base positioning system 306.

The procedure data 504 include data indicative of the specific surgical procedure to be performed on the patient 102. The procedure data 504 can refer to specific requirements of a surgical workspace, e.g., an area around the patient 102 that the surgical tool 108 should be able to access during the surgery, due to the specific surgical procedure to be performed on the patient. A surgical procedure may require a predetermined extent of the workspace.

In some examples, a specific range of motion for the surgical tool 108 can be specified to represent the extent of the workspace. In some cases, the boundaries of the workspace can be delineated to represent the extent of the workspace. In some implementations, an operator can input the data indicative of the extent of workspace. The operator can input the data before the procedure begins and before the base 110 is backdriven by the powered joint 114.

Before the processor 302 executes the process 400 to position the base 110 or during the operation 402 when the processor 302 receives the inputs 500, an operator can demonstrate an extent of the workspace by moving the distal portion of the arm 106 (or of a cannula or surgical tool 108 or other item mounted to the arm 106) within an area representative of the workspace required or otherwise desired for the distal portion of the arm 106 (or of a cannula or surgical tool 108 or other item mounted to the arm 106) during the surgery. For example, an operator can move the surgical manipulator assembly 104 (with or without a tool being held) to indicate the workspace desired, or by moving a substitute of the surgical tool 108 to indicate the workspace desired. Example substitutes include a device that represents an average surgical tool that may be used during the procedure, a device that replicates a proximal portion of the surgical tool 108 but not the entire shaft and end effector, a device that projects a visual indication of locations associated with distal ends of surgical tools that may be used during the procedure, etc. Information about the desired range of motion of the remotely controllable arm 106 or the surgical tool 108 can be derived at least in part from such a demonstration. The pose sensors 309 of the sensor system 308, for example, can generate a signal indicative of a manual demonstration by the operator of a desired workspace, and provide information about the desired range of motion of the remotely controllable arm 106. Sensors (e.g., the pose sensors 309) on the surgical manipulator assembly 104 can detect the physical movement of the surgical manipulator assembly 104 (and/or an item held in the assembly 104, such as the surgical tool 108) and generate signals indicative of the pose of the surgical manipulator assembly 104 (and/or an item held in the assembly 104, such as the surgical tool 108). As the surgical manipulator assembly 104 (and/or an item held in the assembly 104, such as the surgical tool 108) is moved, the processor 302 receives the procedure data 504 including these sensor signals and can then process these sensor signals to determine the extent of the workspace demonstrated by the operator.

The equipment data 506 include data indicative of specifications of the equipment to be used during the surgery. The equipment data 506 can include data that specifies a range of motion for each of the joints of the surgical manipulator assembly 104. The range of motion can be a structural or mechanical limitation. The ranges of motion indicated in the equipment data 506 can include ranges of motion for passive joints, active joints, or both.

For a given joint, the range of motion for the joint can refer to the amount of motion possible between two links connected by the joint. For a revolute joint, the equipment data 506 can specify a value for the range of motion that is between, for example, 90 degrees and 180 degrees (e.g., the range of motion of the joint is 90 degrees, 135 degrees, or 180 degrees). For a prismatic joint, the equipment data 506 can specify a value for the range of motion that is between, for example, 10 centimeters and 30 centimeters (e.g., the range of motion of the joint is 10 centimeters, 20 centimeters, or 30 centimeters). Other ranges of motion beyond those specified herein may be appropriate depending on the configuration of the remotely controllable arm 106 and the setup assembly 109.

The equipment data 506 can further indicate the structure of the remotely controllable arm 106 and the setup assembly 109. For example, the equipment data 506 can specify the number of joints, the types of each joint, the length of links of the remotely controllable arm 106, and other parameters pertaining to the structure of the remotely controllable arm 106.

The equipment data 506 can also include information pertaining to the type of the surgical tool 108 mounted to the remotely controllable arm 106. The type of the surgical tool 108 may affect, for example, an extent of the workspace and an amount of torque necessary to perform an operation. The type of the surgical tool 108 can be manually inputted by an operator. In some examples, the surgical tool 108 may include a detectable tag that indicates the type of the surgical tool 108.

The pose data 508 include data indicative of poses of the joints, links, the surgical tool, and other components of the surgical manipulator assembly 104. The pose data 508 includes the initial pose of each of the joints and/or links of the remotely controllable arm 106, the initial pose of each of the joints and/or links of the setup assembly 109, the initial pose of distal portion of the arm 106 (and/or of a cannula or surgical tool 108 or other item mounted to the arm 106), and the initial pose of the base 110. When the processor 302 executes the process 400 to position the base 110, as the base 110 is moved, the pose sensors 309 can generate signals responsive to motion of the base 110. During the surgery, based on the signals from the pose sensors 309, the processor 302 can control the remotely controllable arm 106 to maintain the position of the distal portion of the arm 106 (or of a cannula or surgical tool 108 or other item mounted to the arm 106) relative to the reference (such as a reference including the reference point 116) in accordance to remote center of motion methods described herein.

The operator data 509 includes data pertaining to the surgical team, e.g., the operators, carrying out the surgical procedure. The operator data 509 includes, for example, information related to the capabilities, preferences for surgical equipment layout, levels of experience, levels of skill, and other operator-specific attributes. In some examples, an operator profile is created for each of the operators before the surgical procedure. A surgical team profile alternatively or additionally is created for a particular surgical team.

The obstacle data 510 include data indicative of poses or positions of the patient 102 and obstacles in the surgical environment 10 relative to the surgical manipulator assembly 104. In some examples, the obstacle data 510 can include a map of the surgical environment 10 inputted by the operator. The map can include locations of potential obstacles within the surgical environment 10, such as other pieces of equipment of the surgical system 100. The obstacle data 510 alternatively or additionally includes data from the obstacle detection sensors 314. As the remotely controllable arm 106, the setup assembly 109, and/or the base 110 are moved within the surgical environment 10, the obstacle detection sensors 314 can generate signals indicative of positions, orientations, or poses of obstacles within the surgical environment 10.

The patient data 512 include data indicative of patient-specific characteristics. The patient data 512 can include data indicative of patient habitus and patient geometry. In some examples, the operator inputs the patient habitus and the patient geometry. In some cases, an imaging device can produce images that can be analyzed by the processor 302 to determine the patient habitus and the patient geometry. The imaging device may be inserted into the patient 102 before the base 110 repositioned during the process 400. The endoscope can produce images usable for estimating the patient habitus and the patient geometry. In some examples, the patient data 512 can also include data indicative of the pose of the patient 102 relative to the remotely controllable arm 106 and/or the pose of the operating table 134 relative to the remotely controllable arm 106. The patient data 512 can include pre-operative images, such as x-ray images, x-ray computed tomography images, magnetic resonance imaging scans, and the like. In some cases, the patient data 512 includes intraoperative images or surface scans.

The port data 514 include data indicative of characteristics of the access port on the patient 102. The port data 514 can indicate a position and orientation of the access port. The processor 302 can use the port data 514 to determine the reference relative to which the surgical tool 108 is maintained in position and/orientation when the base positioning system 306 repositions the base 110. In some implementations, the port data 514 is based on a pose of the controllable arm 106 when a cannula is docked, when an operator indicates readiness for repositioning of the base, when a surgical tool is mounted, etc. In some implementations, a component such as the cannula 158 or the surgical tool 108 is inserted through the access port on the patient 102, and the processor 302 can determine the position and orientation of the access port based on signals from sensors on the remotely controllable arm 106.

In some examples, the port data 514 can be inputted by the operator. If the surgical tool 108 is not inserted into the access port before the processor 302 executes the process 400 to position the base 110, the processor 302 can select the reference based on the inputted port data 514. In some implementations, the reference is selected such that the surgical tool 108 can be positioned and oriented to be easily inserted into the access port after the positioning of the base 110 is complete. In particular, the surgical tool 108 can be in a retracted position during the positioning of the base 110 and then translated axially to an insertion position such that the reference includes a reference point 116 that corresponds to the position of the access port.

If the surgical tool 108 is in the retracted position during the positioning of the base 110, as described in greater detail herein, the surgical tool 108 can be held in place through other mechanisms. For example, as described with respect to FIGS. 7 and 8, an operator can manually fix the surgical tool 108 within the surgical environment 10, or a mechanical fixture can be used or operated to fix the surgical tool 108 within the surgical environment 10.

After receiving (402) the inputs, the processor 302 optionally generates (404) one or more indices based on the inputs. The processor 302 can compute functions that each represent one of the indices. One or more of the indices can be selected, e.g., by the operator or in accordance to a default setting, to be optimized by the processor 302. The processor 302 can then optimize the functions of the selected indices, as described in greater detail with respect to operation 406.

Each of the indices generated at the operation 404 can represent an optimization goal for the processor 302. The indices can refer to values to be optimized when the base positioning system 306 repositions the base 110. Each index generated by the processor 302 during the operation 404 can be a value based on one or more of the inputs. The number of indices generated may depend on the number of degrees of freedom, in particular, the number of redundant degrees of freedom. In this regard, the indices generated at the operation 404 can represent the indices for the current configuration of the surgical manipulator assembly 104 while the base 110 is being repositioned. The values for the indices may change as the base 110 and the joints are moved during the repositioning of the base 110.

Based on the inputs and/or the one or more indices, the processor 302 determines (406) an optimum pose and an optimality score for the current pose of the surgical manipulator assembly 104. The processor 302 can determine a range of optimum poses or optimum positions for the base 110. The range of optimum poses or optimum positions can be represented as the optimal base location envelope 122. The optimal base location envelope 122 can correspond to a range of three-dimensional positions and orientations considered optimal for the base 110. In some implementations, the optimal base location envelope 122 corresponds to a range of optimal two-dimensional positions along a plane parallel to the floor surface 20. In some examples, the optimal base location envelope 122 includes multiple optimal positions having a maximum optimality score. The processor 302 can compute the optimal pose, the optimum poses, and/or the optimal base location envelope 122 based on the inputs 500. The processor 302 can generate functions for the values of the indices at the operations 404 and execute optimization strategies that use the functions to optimize each of the indices. The optimization strategies include, for example, a gradient descent-based optimization strategy, a least squares-based optimization strategy, or other appropriate strategies. The processor 302 can compute a solution to the functions in which the solution represents the optimal base pose or the optimal range of poses for the base 110 using the given optimization strategies. The optimization strategies enable the processor 302 to compute an optimality score representing the optimality of the current pose of the base 110. In some examples, the optimality score represents a proximity of the current pose of the surgical manipulator assembly 104 to the optimal base pose or the optimal base location envelope 122.

In some examples, the processor 302 selects a single index as a primary goal and then computes a solution using the optimization strategies to optimize the index. When the solution is under-constrained, the solution provided by the processor 302 may represent a subset of states available for the remotely controllable arm 106. To identify the specific commands to be transmitted to the joints of the remotely controllable arm 106 when a primary solution is under-constrained, the processor 302 can include a module that acts as a subspace filter to select a desired state of the remotely controllable arm 106 from among the subset of states. The subspace filter can also select a set of commands for the joints of the remotely controllable arm 106 to move the joints such that the remotely controllable arm 106 is placed in the desired state. Advantageously, the selected commands can be used to serve a second goal, e.g., to optimize a second index. In some examples, multiple indices are selected, and a weight is assigned to each of the selected indices. The weight is indicative of a priority of that index relative to other selected indices. For example, operators may determine that the procedure type and patient characteristics have greater priority for optimization than operator preference. Examples of optimization of multiple goals are described in the '229 patent, the entirety of which is incorporated herein by reference.

Each index may have a range of values considered to be optimal. When the index is within the optimal range of values, the remotely controllable arm 106 and the surgical tool 108 are in states beneficial to the operation of the surgical manipulator assembly 104 as compared to states of the remotely controllable arm 106 and the surgical tool 108 when the index is not within the optimal range of values. The optimal range of values for an index can correspond to any value of the index above a threshold value. The threshold value can be programmed as a default value, a percentage of a maximum or minimum value of the index, or can be inputted by the operator.

Various indices are described herein. These indices may be functions of one or more of the inputs 500. The example uses of combinations of the data 504, 506, 508, 510, 512, 514 described herein to compute the indices are not intended to be limiting. For a given implementation of the process 400, the processor 302 may generate one or more of the indices. In some implementations, the processor 302 does not generate indices, but rather, directly compares one or more of the inputs 500 to compute the optimality score.

The processor 302 optionally generates and optimizes a range of motion index based on the range of motion available for each of the joints. The range of motion index may be computed based on, for example, the equipment data 506 and the pose data 508. For example, for a revolute joint that can rotate in two directions about an axis, the processor 302 can determine an amount of motion available in each of the two directions. The processor 302 can determine a target ranges of joint states for each of the joints of the remotely controllable arm 106. In some cases, it can be beneficial for the joint to be positioned such that the joint can move in both directions a substantially equal amount, whereas in some examples, it can be desirable to maximize the amount of motion available in a single direction. The target range of joint states thus can be a subset of the available range of joint states for a given joint. The processor 302 can compute the range of motion index by considering range of motion requirements for each of the joints of the remotely controllable arm 106.

The range of motion index alternatively or additionally considers the range of motion of the surgical tool 108. In particular, the processor 302 can compute the range of motion index based on whether the surgical tool 108 has sufficient range of motion to reach the relevant portions of the anatomy for the specific surgical procedure. In this regard, the processor 302 may also use procedure data 504 in computing the range of motion index.

When the base 110 is being repositioned, the pose sensors 309 can generate signals responsive to motion of the joints and/or links of the remotely controllable arm 106, thereby updating the pose data 508. Upon receiving these signals, the processor 302 can update its determination of the range of motion index based on the new pose of each of the joints and/or links of the remotely controllable arm 106.

The processor 302 optionally computes a stability index. The processor 302, for example, computes the stability index based on the pose data 508 to determine the stability of the distal portion of the arm 106 (or of a cannula or surgical tool 108 or other item mounted to the arm 106) in the current pose. The stability index can be computed based on an amount of movement of the distal portion of the arm 106 (or of a cannula or surgical tool 108 or other item mounted to the arm 106) while the base 110 is being repositioned. For example, during the positioning of the base 110, if the pose sensors 309 detects large movement distance, speed, or acceleration of the distal portion of the arm 106 (or of a cannula or surgical tool 108 or other item mounted to the arm 106), the processor 302 can determine that the stability index is suboptimal.

The processor 302 alternatively or additionally computes a smoothness index. The smoothness index is indicative of the motion performance of the surgical tool 108 and, in some cases, the motion performance of some or all of the joints of the remotely controllable arm 106. The processor 302 can estimate the motion performance by determining a resolution of motion of the surgical tool 108 that is possible for the current pose of the remotely controllable arm 106 and the surgical tool 108. For example, for a particular joint, actuation of the joint by an increment (e.g., a given applied voltage or current) may result in an amount of motion of the surgical tool 108 that depends on the pose of each of the joints of the remotely controllable arm 106 and the pose of the surgical tool 108. In some implementations, the smoothness index is computed based on the spatial resolution achievable as a function of pose and joint sensor position resolution. The smoothness index can account for the size of the motion caused by the increment (e.g., an incremental voltage or current) applied. In this regard, a smaller motion of the surgical tool 108 from a given applied increment can result in improved motion performance of the surgical tool 108 and greater smoothness of motion. The processor 302 can compute the smoothness index based on, for example, the equipment data 506 and the pose data 508.

The processor 302 optionally computes a torque index for the surgical tool 108. The torque index can be indicative of a torque that the remotely controllable arm 106 can exert on the surgical tool 108. In some implementations, the surgical procedure may require that the remotely controllable arm 106 be able to manipulate the surgical tool 108 with a minimum torque necessary to perform the surgical procedure. It may be beneficial in these cases to maximize the torque achievable by the surgical tool 108. The achievable torque, however, can depend on the positions and orientations of the joints relative to the surgical tool 108 as well as the position of the base 110 relative to the surgical tool 108. The processor 302 can compute the torque index based on, for example, the procedure data 504, the equipment data 506, and the pose data 508.

In some implementations, instead of or in addition to a torque index, a force index indicative of a force that the remotely controllable arm 106 can exert on the surgical tool 108 is computed. Furthermore, the torque index and/or the force index may account for forces and torques on joints of the surgical manipulator assembly 104 such that forces and/or torques on a particular joint can be minimized during motion of the remotely controllable arm 106 within the workspace.

The processor 302 can compute a workspace index representative of the portion of the workspace accessible by the surgical tool 108 for the current state of the remotely controllable arm 106. The processor 302 can compute the workspace index based on the workspace indicated in the procedure data 504, e.g., demonstrated by the operator. The base positioning system 306 can be controlled by the processor 302 to reposition the base 110 to optimize the workspace index. The processor 302 can control the base positioning system 306 based on the signals from the pose sensors 309 indicative of the manual demonstration and the data used to compute the workspace index.

The processor 302 can compute the portion of the workspace accessible by the surgical tool 108 based on the equipment data 506 and the pose data 508 by determining the extent that the surgical tool 108 can be moved given the ranges of motion of the joints of the remotely controllable arm 106. In some implementations, the processor 302 can use the patient data 512 to consider patient geometry and patient habitus in determining the workspace index. In some examples, the processor 302 can base the computation of the workspace index on the port data 514, in particular, on the location and orientation of the access port on the patient 102. In some examples, the patient data 512 includes images of the patient physiology that, when used in combination with the procedure data 504, can be used to estimate required instrument workspace bounds.

The processor 302, in some examples, computes a singularity index that indicates the likelihood that any joint of the remotely controllable arm 106 may be actuated to a state corresponding to a kinematic singularity. For example, for the remotely controllable arm 106, a kinematic singularity occurs when the remotely controllable arm 106 is in a state in which it loses its ability to move, or to apply forces, in one or more directions. The processor 302 can determine potential kinematic singularities based on the equipment data 506. For example, the kinematic singularities for each of the joints may depend on the present configuration of the remotely controllable arm 106.

The processor 302 optionally estimates an obstacle index based on the pose data 508 and the obstacle data 510. The obstacle index represents a likelihood that the remotely controllable arm 106 may collide with nearby obstacles. In this regard, using the obstacle data 510, the current pose of the remotely controllable arm 106, and the procedure data 504, the processor 302 can compute the obstacle index to determine whether the remotely controllable arm 106 may collide with a nearby obstacle if the surgical tool 108 is to be able to access the extent of the workspace specified in the procedure data 504.

The processor 302 alternatively or additionally computes a patient force index indicative of an amount of risk of harm to the patient. For example, the patient force index may be computed based on the pose data 508, the patient data 512, and the port data 514 and may be indicative of an amount of torque or force that may be exerted on a wall of the patient 102 around the vicinity of the access port. The processor 302 can use the patient force index to determine if the remotely controllable arm 106 or the base 110 are being moved in a manner that may place force exceeding a desired amount on the tissue of the patient 102.

In some implementations, the processor 302 computes a dexterity index that represents a dexterity of the surgical tool 108 in the given pose of the surgical tool 108. The dexterity index is, for example, an aggregate index that accounts for one or more of the smoothness index, the torque index, the workspace index, and the singularity avoidance index. In some cases, the dexterity index is computed based on a manipulability index and/or a Jacobian condition number for the joints of the surgical manipulator assembly 104.

In some implementations, an optimization strategy for a surgical operation is based on data from previous surgical operations. The data from the previous surgical operations include, for example, inputs collected during the previous surgical operations, indices determined during the previous surgical operations, and/or scores determined during the previous surgical operations.

If the optimality score is greater than a threshold optimality score (operation 408), the processor 302 optionally outputs (operation 410) a signal that activates an indication signifying that the positioning of the base 110 is complete. The indication is, for example, a visual, tactile, or audible indication. In some examples, the indication is presented on a graphic display that the operator views during the positioning of the base 110. In some examples, the indication is positioned on the surgical manipulator assembly 104 or on the base 110.

If the optimality score is less than (operation 412) the threshold optimality score, the processor 302 outputs (operation 414) control signals to reposition the base. The processor 302, for example, outputs (operation 414) control signals to cause the base positioning system 306 to reposition the base 110. The processor 302, for example, transmits the control signals, and the base positioning system 306 responds to the control signals by activating the powered joint 114 to backdrive the base 110 to move toward the optimum base pose or toward the optimal base location envelope 122. The joint control mechanism 304 is controlled, for example, to operate the powered joint 114 to exert a torque. The torque causes movement of the base 110 without causing substantial movement of the surgical tool 108. In some cases, the base 110 is locked from moving about the surgical environment 10.

In some implementations, the control signals release the base 110 to enable movement of the base 110 about the surgical environment 10. The control signals then cause the joint control mechanism 304 to operate the joints of the remotely controllable arm 106 to reposition the base 110.

In some implementations, as described herein, the control signals cause an electronically addressable tool fixation mechanism to fix and externally maintain the position and/or orientation of the distal portion of the arm 106 (or of a cannula or surgical tool 108 or other item mounted to the arm 106) within the surgical environment 10. The tool fixation mechanism is, for example, activated to cause the position and/or orientation of the distal portion of the arm 106 (or of a cannula or surgical tool 108 or other item mounted to the arm 106) to be maintained relative to the reference.

In some implementations, while outputting (414) the control signals, the processor 302 activates a braking mechanism to stop movement of the base 110 before the base 110 has moved into the optimal base location envelope 122. The processor 302 controls, for example, the brakes or braking mechanism based on changes in the value of the patient force index. In some cases, the position and/or orientation of the distal portion of the arm 106 (or of a cannula or surgical tool 108 or other item mounted to the arm 106) is maintained by the reaction force from the tissue of the patient 102. The processor 302 determine that force exceeding a desired amount is being applied to the tissue of the patient 102 based on the patient force index. The processor 302 may then issue an alert to an operator that some manual repositioning of the joints, the base 110, or the patient 102 may be required to reduce the force on the tissue of the patient 102.

In some implementations, during the outputting (414) of the control signals, the processor 302 determines that the stability index indicates that the distal portion of the arm 106 (or of a cannula or surgical tool 108 or other item mounted to the arm 106) is not sufficiently stable. The processor 302, for example, determines that forces keeping the distal portion of the arm 106 (or of a cannula or surgical tool 108 or other item mounted to the arm 106) in place are not high enough to inhibit movement of the distal portion of the arm 106 (or of a cannula or surgical tool 108 or other item mounted to the arm 106) when the powered joint 114 is actuated. The processor 302 determines that the forces are not sufficiently high, for example, based on the pose data 508. In some cases, force or torque exerted at the distal portion of the arm 106 (or of a cannula or surgical tool 108 or other item mounted to the arm 106) does not proportionally increase with the torque applied by the powered joint 114 if the distal portion of the arm 106 (or of a cannula or surgical tool 108 or other item mounted to the arm 106) is not sufficiently stabilized.

Alternatively or additionally, the processor 302 determines based on the pose data 508 that the distal portion of the arm 106 (or of a cannula or surgical tool 108 or other item mounted to the arm 106) is moving relative to the reference (such as a reference point 116, one or more reference directions, a reference frame, etc.). For example, the processor 302 can determine that excessive movement is occurring based on signals from the pose sensors 309, or the processor 302 can determine that the force or torque at the surgical tool 108 is insufficient based on the pose sensors 309, e.g., force or torque sensors. Excessive movement of the surgical tool 108 can cause the stability index to indicate that the surgical tool 108 is not sufficiently stable. For example, the surgical tool 108, when considered unstable, can move between, for example, 1 millimeter and 20 millimeters (e.g., 1 to 10 millimeters, 5 to 15 millimeters, 10 to 20 millimeters, 15 to 20 millimeters, etc.), when the powered joint 114 is actuated to backdrive the base 110. Upon determining that the surgical tool 108 is not stable, the processor 302 can stop further repositioning of the base 110 and can issue an alert to the operator that the surgical tool 108 needs to be stabilized before the powered joint 114 is activated again.

Alternatively or additionally, the processor 302 determines if the position and/or orientation of the distal portion of the arm 106 (or of a surgical tool 108 or other device held in the arm 106) is not maintained relative to the reference. And, if the position and/or orientation is not maintained within a threshold or other maintenance criteria, the processor 302 can slow or stop further repositioning of the base 110. The processor 302 can also issue an alert to the operator to provide sufficient external maintenance of the position and/or orientation of the distal portion of the arm 106 (or of a surgical tool 108 or other device held in the arm 106).

After the processor 302 outputs (operation 414) the control signals to backdrive the base 110, the processor 302 can repeat the operations 402, 404, 406, 407, 412, and 414 until the processor 302 determines that the optimality score of the base pose exceeds the threshold optimality score. At that point, the processor 302 can then perform operations 408 and 410 to indicate completion of the positioning of the base 110.

In some implementations, rather than repeating the operations 402, 404, 406, 407, 412, and 414, until the processor 302 determines that the optimality score of the base pose exceeds the threshold optimality score, the positioning of the base 110 is ceased before the optimality score exceeds the threshold optimality score. For example, the operator can provide a user input to override the process 400 and to cause the processor 302 to discontinue repetition of the operations to reposition the base 110. Alternatively, the processor 302 can automatically cease guiding the repositioning of the base 110 in response to a predefined condition being satisfied. The predefined condition can indicate to the processor 302 that the base 110 is unable to be repositioned into the optimal base location envelope 122. For example, if the optimality score does not exceed the threshold optimality score after a predefined amount of time has elapsed after the process 400 is initiated, e.g., 5 to 15 minutes, the processor 302 overrides the process 400. In further examples, the processor 302 determines, based on the obstacle data 510, that there does not exist a path of movement for the base 110 into the optimal base location envelope 122 due to obstacles between the current location of the base 110 and the optimal base location envelope 122. If the repositioning of the base 110 is ceased before the optimality score exceeds the threshold optimality score, the processor 302 can issue an alert indicating that the base 110 is in a sub-optimal position, e.g., is outside of the optimal base location envelope 122.

FIGS. 6A to 6H depict operations 600A to 600H during which a processor controls the powered joint 114 to backdrive the base 110 toward the optimal base location envelope 122. Each of the operations 600A to 600H can include sub-operations performed by an operator 604, a processor (e.g., the processor 302 of the control system 300), or a combination thereof. In some implementations, some or all of the operations 600A to 600H are performed by the processor 302.

Figure 6A:
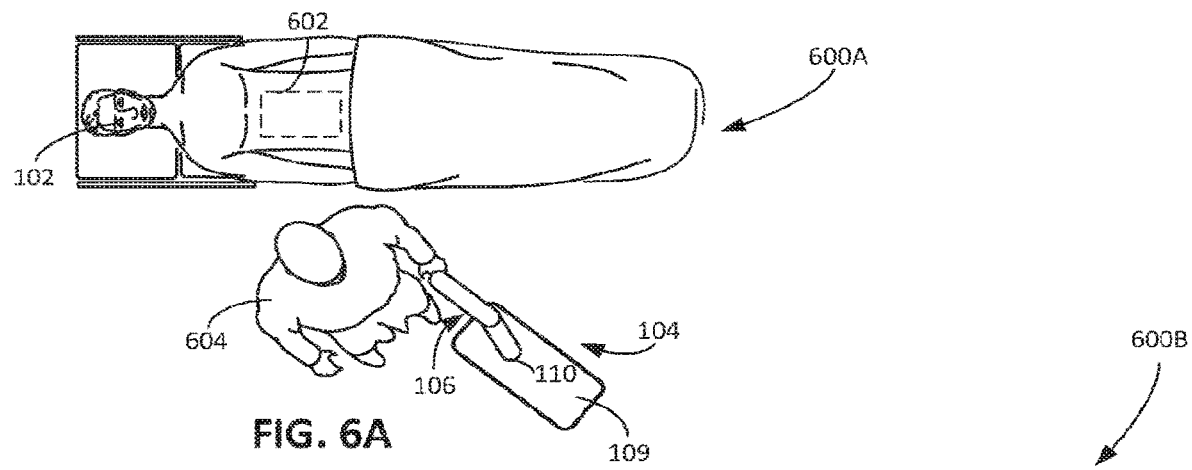
FIGS. 6A to 6H are top views depicting sequential operations for positioning a base of a surgical manipulator assembly adjacent an operating table.
Figure 6B:
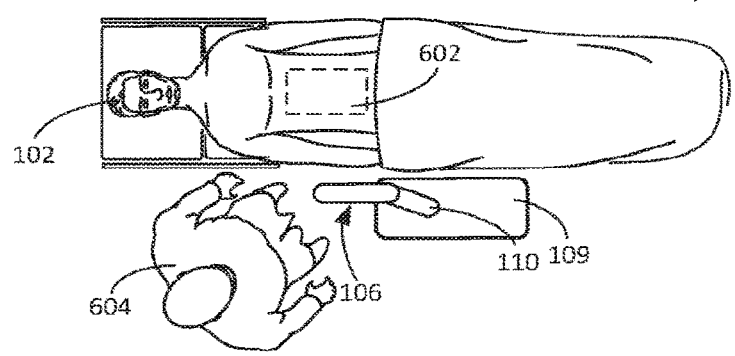

In FIGS. 6A and 6B, respectively, the base 110 is repositioned to be adjacent a workspace 602 around the patient 102. In some examples, during operations 600A and 600B, an operator 604 manually manipulates the setup assembly 109 such that the surgical manipulator assembly 104 is positioned adjacent the workspace 602. The operator 604, for example, pushes or pulls the cart 111 (shown in FIG. 2) of the setup assembly 109 to move the surgical manipulator assembly 104.

As shown in FIGS. 6A and 6B, in some cases, the operator 604 grasps the remotely controllable arm 106 of the surgical manipulator assembly 104 and exerts a force on the remotely controllable arm 106 to pull the surgical manipulator assembly 104, including the base 110, toward an area adjacent the operating table 134. The operator 604 grasps, for example, a distal portion of the remotely controllable arm 106 or grasps the surgical tool (not shown) mounted to the distal portion of the remotely controllable arm 106.

In some cases, in response to the force provided by the operator 604, the powered wheels of the setup assembly 109 are activated by the processor to cause the base 110 to move in the direction of the force exerted by the operator 604 on the remotely controllable arm 106. The powered wheels of the setup assembly 109, when driven, assist the operator 604 to move the surgical manipulator assembly 104 toward the area adjacent the operating table 134. The joints of the remotely controllable arm 106 are, in some cases, locked so that the force that the operator 604 applies to the remotely controllable arm 106 is transmitted directly to the cart 111 of the setup assembly 109. To cause the processor to activate the powered wheels and lock the joints, the operator 604, in some cases, pushes an input button that generates a signal indicating to the processor that the operator 604 is manually repositioning the base 110 by pulling on the remotely controllable arm 106.

Figure 6C:
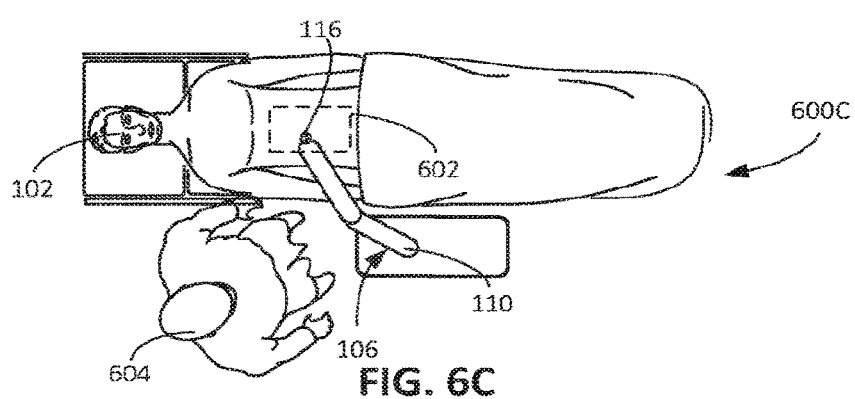

At operation 600B shown in FIG. 6B, the base 110 has been repositioned adjacent to the operating table 134 and the patient 102. The remotely controllable arm 106 is then deployed such that the surgical tool is within the workspace 602 for the surgery, as shown in FIG. 6C. In some examples, the operator 604 manually moves the remotely controllable arm 106 to deploy the remotely controllable arm 106 within the workspace 602. In some examples, joints of the remotely controllable arm 106 are actuated to deploy the remotely controllable arm 106 into the workspace 602.

In some implementations, when the remotely controllable arm 106 is deployed, the operator 604 demonstrates the extent of the workspace 602. The operator 604, for example, manually manipulates the distal portion, instrument holder, or other portions of the remotely controllable arm 106 so that a portion of the remotely controllable arm 106 (or the surgical tool if mounted to the remotely controllable arm 106) is moved through the boundaries of the workspace 602. The processor receives the sensor signals from pose sensors on the remotely controllable arm 106 and then use those signals to estimate the extent of the workspace 602. Other methods of demonstrating the workspace 602 are described herein.

At operation 600C, the reference (such as the reference point 116) is specified. In some examples, at operation 600C, the surgical tool is inserted into an access port on the patient 102, The reference point 116 is defined to corresponds to, for example, a location of the access port. The operator 604 clutches various joints of the remotely controllable arm 106 to manipulate the distal link or other portion(s) of the remotely controllable arm 106 to insert the surgical tool into the access port. Examples of clutching are described in detail in the '223 patent incorporated herein by reference.

In some implementations, a position for defining the reference is provided to the processor in a manner other than by physically placing the surgical tool through the access port. For example, the processor can determine the reference using a point on a component in physical contact with the remotely controllable arm 106, or a point in space that is not mechanically connected or part of a component mechanically connected to the remotely controllable arm 106. For example, if the instrument holder 142 is coupled to the cannula 158 and the cannula 158 is inserted into the patient, the reference can include a reference point 116 located along the cannula 158, such as where the cannula 158 contacts a body wall of the patient. If the instrument holder 142 is decoupled from the cannula 158, the reference can include a reference point 116 associated with where an installed cannula would be if installed. Data for setting the reference may be indicated in other ways in various implementations. In some implementations, the operator manipulates an input device to indicate that the remotely controllable arm 106 is proximate to the access port on the patient 102, the remotely controllable arm 106 is docked to a cannula 158 already inserted into an access port on the patient 102, a cannula 158 held by the remotely controllable arm 106 is inserted into the patient 102, image acquisition and recognition is performed to identify incisions in the patient or guide markings placed on the patient for indicating reference point(s) and/or direction(s), etc.

The position and/or orientation of the surgical tool can be externally maintained and secured within the surgical environment in another manner. In some of these cases, the reference is more likely to correspond to a reference point that does not coincide with the access port on the patient 102. For example, a mechanical fixture can externally maintain the position and/or orientation of the surgical tool relative to a reference including a reference point near or on the mechanical fixture. In some cases, a hand of the operator 604 can grasp the surgical tool to externally maintain the position and/or orientation of the surgical tool relative to a reference including a reference point corresponding to a position of the hand. The processor can select or determine the reference so that the surgical tool can be inserted into the access port after the positioning of the base 110 is complete.

Figure 6D:
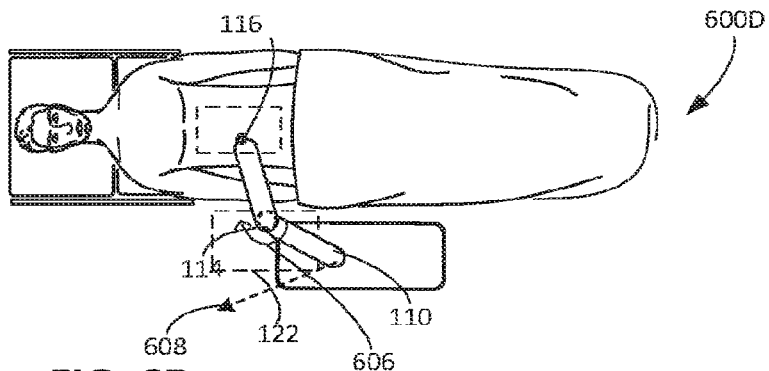
Figure 6E:
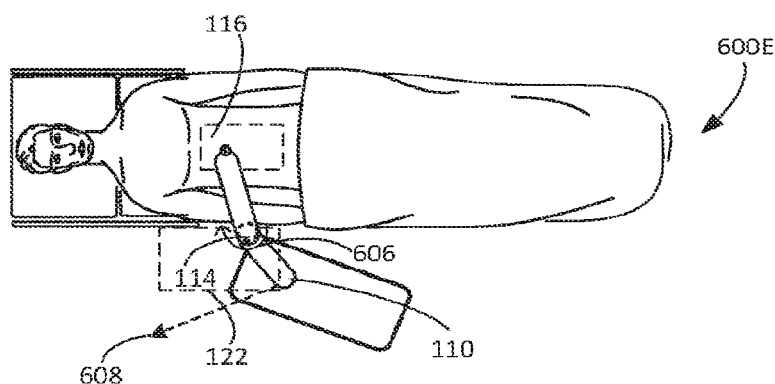
Figure 6F:
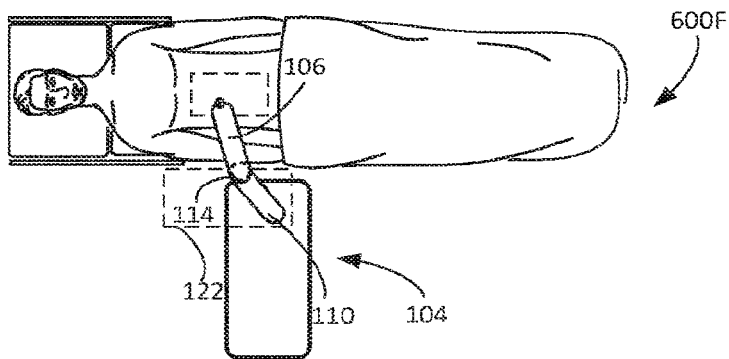

At operation 600D of FIG. 4D, the processor can determine the optimal base location envelope 122 based on received inputs, as described in greater detail with respect to FIGS. 4 and 5. As shown in FIGS. 6D to 6F, at operations 600D to 600F, respectively, the processor controls the base positioning system to move the base 110 toward the optimal base location envelope 122. The base positioning system controls the powered joint 114 in such a manner to cause the base 110 to be backdriven toward the optimal base location envelope 122.

In the examples depicted in FIGS. 6D to 6F, the processor drives the powered joint 114 in a drive direction 606. In some cases, a braking mechanism for the joints of the setup arm (shown in FIG. 2) is selectively activated or released to inhibit or enable movement of the base 110 relative to the floor surface 20. In some cases, a braking mechanism for the cart 111 of the setup assembly 109 is selectively activated or released to inhibit or enable movement of the cart 111 across the floor surface.

In some implementations, the remotely controllable arm 106 includes joints positioned in kinematic series between the powered joint 114 and the base 110, the processor can control the joint control mechanism to lock or brake those joints. When the joints are locked, the torque exerted by the powered joint 114 is transferred directly to the base 110 to cause the base 110 to move relative to the floor surface 20.

When the processor drives the powered joint 114 in the drive direction 606, the base 110 is driven in a repositioning direction 608 toward the optimal base location envelope 122. As shown in FIGS. 6D to 6F, the base 110 then rotates about the powered joint 114. The base 110, for examples continues to rotate until the base 110 is situated within the optimal base location envelope 122. In some implementations, when the base 110 enters the optimal location envelope 122 at during operation 600F, an alert is issued indicating that the repositioning of the base is complete.

After the repositioning of the base 110 has been successfully completed, the surgical operation can commence. The surgical tool can be inserted into the access port on the patient 102. A surgeon can remotely controllable the remotely controllable arm 106 of the surgical manipulator assembly 104 to control the surgical tool to perform the surgery.

During the surgery, in some implementations, a second repositioning of the base 110 may be beneficial to reposition the base 110 in a more optimal position due to changes in the inputs received by the processor. In some cases, the operator 604 may issue a request to the processor to reposition the base 110 again. In some examples, the processor detects that a second repositioning and then requests that the operator 604 provide confirmation that the processor should perform a second positioning of the base 110 using the base positioning system. For example, an obstacle can be placed adjacent the surgical manipulator assembly 104 during the procedure after the initial repositioning is complete. The position of the base 110 from the initial repositioning process may result in a high likelihood that the remotely controllable arm 106 collides with the obstacle 612 during the surgery.

Figure 6G:
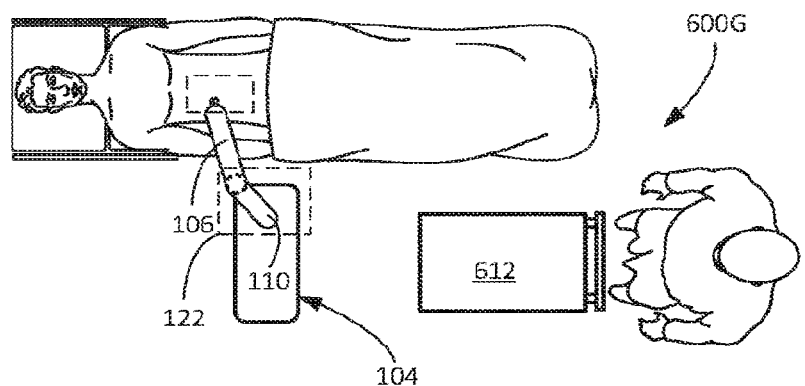
Figure 6H:
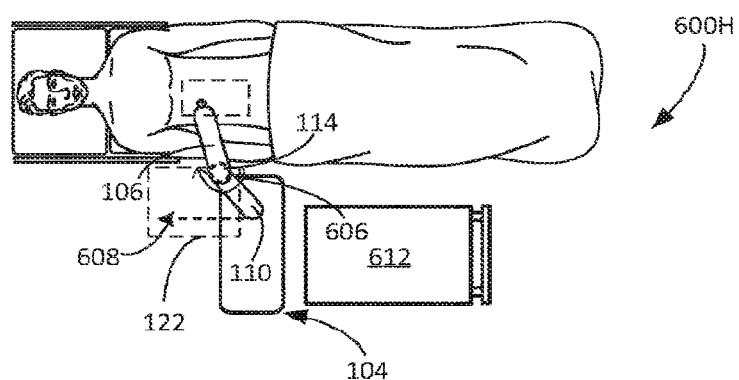

As shown in FIG. 6G, at operation 600G, the optimal base location envelope is an initial optimal base location envelope 122 that does not account for an obstacle 612, e.g., an accessory cart. In FIG. 6G, the obstacle 612 is sufficiently far from the surgical manipulator assembly 104 such that collision between the remotely controllable arm 106 and the obstacle 612 is unlikely. However, as shown in FIG. 6H, at operation 600H, the obstacle 612 is moved to a position adjacent the surgical manipulator assembly 104, thus increasing the likelihood of collision.

As described with respect to FIGS. 3 to 5, the surgical manipulator assembly 104 includes obstacle detection sensors that can be used to detect the obstacles near the remotely controllable arm 106 of the surgical manipulator assembly 104. Upon detecting the obstacle 612, the processor can determine that the likelihood of collision is sufficiently large that the remotely controllable arm 106 should be repositioned away from the obstacle 612. While it may be possible that the joints can be actuated without movement of the base 110 to avoid collision between the remotely controllable arm 106 and the obstacle 612, in some examples, it may be beneficial to reposition the base 110 a second time to achieve other goals, as described with respect to FIGS. 4 and 5. For example, the second repositioning of the base 110 may beneficially improve the range of motion of the joints of the remotely controllable arm 106 in light of the new obstacle 612, which may impede the range of motion of some of the joints if the base 110 is not repositioned. As shown in FIG. 6H, the processor during operation 600H can compute a new optimal base location envelope 122 that accounts for the new obstacle. The processor then controls the powered joint 114 to apply a torque in a drive direction 606 to reposition the base 110 again. The torque in the drive direction 606 can cause the base 110 to move in the repositioning direction 608 toward the new optimal base location envelope 122.

Additional Implementation Alternatives

The systems described above may optionally include one or more of the following features in addition to, or in place of, the features discussed above.

While the arm 106 is described as being remotely controllable, in some implementations, the arm 106 is controlled by an operator at a location within the same room as the arm 106. For example, if the arm 106 is used during a medical procedure, the operator can control the arm 106 from a bedside of the patient.

The surgical system 100 represents an example of a surgical system that can include methods, systems, and devices that facilitate positioning of the base 110 through activation of a powered joint to backdrive the base 110. The surgical system 100 and the methods described herein can be modified to include alternative or additional features. Some features of the surgical system 100 may also be omitted. In some cases, these modifications can additionally change the operation of the surgical system 100, e.g., the operations 402, 404, 406-408, 410, 412, and 414 and the operations 600A to 600H.

While an optimal location envelope has been described for the base 110, in some implementations, an optimal location envelope is computed for joints or other movable components of the surgical manipulator assembly 104. In some cases, one or more of the joints of the remotely controllable arm 106 and the setup assembly 109 includes optimal location envelopes. A given joint is, for example, backdrivable by a powered joint positioned kinematically distally to the given joint. In some cases, the processor 302 determines an optimal location envelope for the cart 111, and the cart 111 is backdriven by a powered joint positioned kinematically distally to the cart 111. In some implementations, the processor 302 operates powered joints of the remotely controllable arm 106 to position each of the joints of the remotely controllable arm 106 within a target range of joint states. The processor 302, for example, sequentially repositions each of the joints. In some cases, the processor 302 repositions each of the joints and then repositions the base 110. In some cases, a distinct powered joint is operated to reposition each joint.

Many of the above example describe the position of the surgical tool 108 relative to the reference as being maintained during the repositioning of the base 110. However, the same techniques may be used to maintain the position and/or orientation of the distal portion of the arm 106 (or of an item held in the distal portion of the arm 106). In some examples, the position and/or orientation of a distal portion of the remotely controllable arm 106 is maintained relative to a reference such as the reference point 116. The distal portion of the remotely controllable arm 106 can be externally maintained while the powered joint 114 is controlled to backdrive the base 110. In some implementations, an operator can grasp the distal portion of the remotely controllable arm 106 and hold the distal portion in place when the powered joint 114 is actuated to position the base 110. In some examples, the distal portion of the remotely controllable arm 106 can be placed into a fixture to hold the distal portion of the remotely controllable arm 106 in place while the powered joint 114 is driven. In some cases, the stiffness of the patient's body wall is sufficient to externally maintain the position and/or orientation of the surgical tool such that a separate fixture may not be necessary.

In some examples, the position of the distal portion of the arm 106 (or of a cannula or surgical tool 108 or other item mounted to the arm 106) can be maintained by inertia of the surgical tool 108 (if present) or inertia of joints and links distal to the powered joint 114. For example, the inertia of the joints and links distal to the powered joint 114 along with the inertia of the surgical tool 108 may be large enough to resist movement of the torque applied by the powered joint 114. The inertia of the joints and links proximal to the powered joint 114 along with the inertia of the base 110 can be less than the inertia distal to the powered joint 114. As a result, the torque applied by the powered joint 114 causes the base 110 to be backdriven. The base positioning system 306 can therefore control the powered joint 114 to backdrive the base 110 without using a mechanical fixture or other device external to the surgical manipulator assembly 104 to maintain the position and/or orientation of the distal portion of the arm 106 (or of a cannula or surgical tool 108 or other item mounted to the arm 106).

Figure 7:
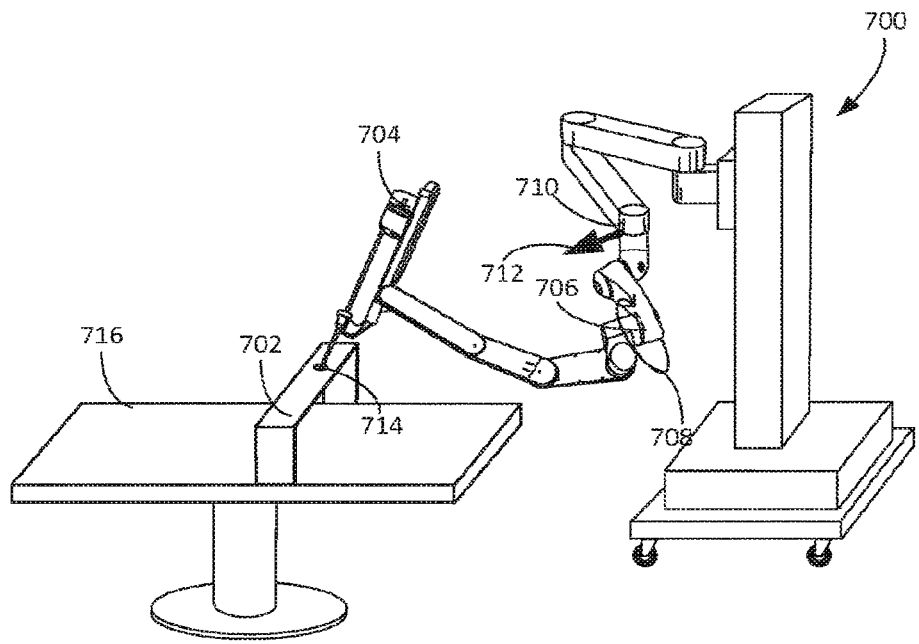
FIG. 7 is a perspective view of a fixture to maintain a position of a tool.

In some implementations, a mechanical fixture externally maintains the position and/or orientation of the distal portion of the arm 106 (or of a cannula or surgical tool 108 or other item mounted to the arm 106). The mechanical fixture is, for example, an electronically addressable tool fixation mechanism that is controllable by the processor 302. The mechanical fixture is activated to fix the position of the distal portion of the arm 106 (or of a cannula or surgical tool 108 or other item mounted to the arm 106) relative to the floor surface 20. For instance, as shown in FIG. 7, a surgical system 700 includes a mechanical fixture 702 that holds a surgical tool 704 when a powered joint 706 is driven in a drive direction 708. The base 710 is backdriven by the powered joint 706 such that the base 710 moves in a repositioning direction 712.

The mechanical fixture 702 maintains the position and/or orientation of the distal portion of the arm 106 (or of a cannula or surgical tool 108 or other item mounted to the arm 106) so that the surgical tool 704 does not move when the powered joint 706 is driven in the drive direction 708. The mechanical fixture 702 serves to maintain the position and/or orientation of the surgical tool 704 relative to a reference (such as a reference including reference point 714) on the mechanical fixture 702. The mechanical fixture 702 can be part of an operating table 716. In some examples, the mechanical fixture 702 is an independent fixture that is removed from the vicinity of the operating table 716 after the positioning of the base 710.

The mechanical fixture 702 is, in some examples, be operated by a processor (e.g., the processor 302) or a base positioning system (e.g., the base positioning system 306). Before the base positioning system drives the powered joint 706, the base positioning system can activate the mechanical fixture 702 to cause the mechanical fixture to lock the surgical tool 704. Upon activation, the mechanical fixture 702 inhibits movement of the surgical tool 704 relative to the mechanical fixture 702. However, the mechanical fixture 702 is alternatively manually secured to the surgical tool 704 and then manually removed from the surgical tool 704 when the surgery begins.

Figure 8:
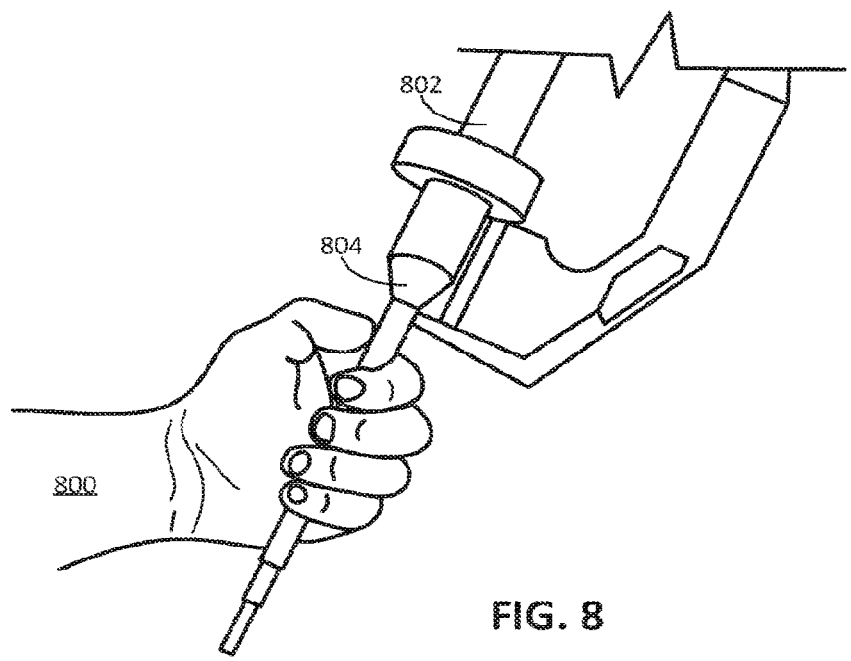
FIG. 8 is a perspective view of a hand holding a cannula to maintain the position of a distal portion of the manipulator arm supporting the cannula.

As shown in FIG. 8, a hand 800 of the operator can alternatively be used to secure the position of the distal portion of the arm 106, or something mounted to the distal portion of the arm 106 such as a cannula or a surgical tool 802. The hand 800 grasps the surgical tool 802 or a cannula 804 with a sufficient amount of force to prevent the surgical tool 802 from moving when a powered joint is activated. During the backdriving of the base, if the hand 800 releases the surgical tool 802, the processor can determine the surgical tool 802 has been released. The processor can issue an alert indicating to the operator should secure the position of the surgical tool 802, e.g., by grasping the surgical tool 802.

While the powered joint 114 is depicted as being configured to exert a torque about an axis offset from a vertical axis extending from the floor surface 20, in some examples, the powered joint 114 may be positioned such that the torque exerted by actuation of the powered joint 114 is parallel to the vertical axis. In such examples, a greater portion of the torque transmitted from the powered joint 114 to the base 110 is capable of translating the base 110 relative to the floor surface 20.

In some implementations, the setup joints and the manipulator joints of the remotely controllable arm 106 can include a combination of revolute and prismatic joints different from the combination described with respect to FIG. 2. Each of the joints can provide translational degrees of freedom, rotational degrees of freedom, or combinations thereof. A joint may include multiple rotational degrees of freedom, e.g., rotation about multiple independent axes. A joint may include multiple translational degrees of freedom, e.g., translation along multiple independent axes. For example, while the setup joints 150$b$-150$c$ and 156$a$-156$g$ have been described as revolute joints, in some examples, one or more of these joints 150$b$-150$c$, 156$a$-156$g$ can allow for translational degrees of freedom, thus enabling relative translation between links of the setup arm 138 and the remotely controllable arm 106. The joint 150$a$, while described as a prismatic joint, can be a revolute joint that permits the remotely controllable arm 106 to pivot relative to the base 110. In some cases, a joint may allow for both relative rotation and translation between links. The remotely controllable arm 106 can include fewer or additional links and joints depending on the degrees of freedom desired for the given application.

The type of joints for the remotely controllable arm 106 and the setup arm 138 can vary in different implementations. In some examples, the remotely controllable arm 106 includes only powered joints while the setup arm 138 includes only passive joints. In some implementations, the surgical manipulator assembly 104 includes the remotely controllable arm 106 but does not include the setup arm 138. For example, the remotely controllable arm 106 includes a single powered joint that couples the remotely controllable arm 106 to the base 110. The processor 302 can selectively activate the single powered joint to drive the base 110 toward the optimal base location envelope 122. In some implementations, the remotely controllable arm 106 includes two or more powered joints. The processor 302 selectively activates one of the powered joints to backdrive the base in one direction and can selectively activate the other of the powered joints to backdrive the base in another direction. In some cases, the processor 302 can selectively activate a combination of joints to backdrive the base 110 to cause rotation of the base 110, translation of the base 110, or a combination thereof.

In some cases, the remotely controllable arm 106 and the setup arm 138 include a selectively releasable passive joint. The selectively releasable passive joint can include, for example, a braking mechanism that maintains the position of the passive joint. In this regard, the remotely controllable arm 106 can include the powered joint 114 and the selectively releasable passive joint. The selectively releasable passive joint can be positioned between the powered joint 114 and the base 110. To ensure that torque from the powered joint 114 transfers to the base 110, the processor 302 can lock the selectively releasable passive joint while driving the powered joint 114.

While the surgical system 100 depicted in FIG. 1 shows a single surgical manipulator assembly 104, in some examples, the surgical manipulator assembly 104 may be one of multiple surgical manipulator assemblies, each of which includes a remotely controllable arm. Each of the remotely controllable arms can include a surgical tool, and the bases of each of the surgical manipulator assemblies can be backdriven toward optimal base location envelopes using the methods described herein. The repositioning of each of the bases can occur while the positions and/or orientations of the surgical tools mounted to the arms are maintained relative to associated references in the surgical environment. In some cases, the processor can detect other surgical manipulator assemblies using the obstacle detection sensors and consider the other surgical manipulator assemblies to be obstacles within the surgical environment. In this regard, the obstacle data used by the processor to backdrive the base of the surgical manipulator assembly can include the position of the other surgical manipulator assemblies.

In some examples, rather than being a surgical manipulator assembly 104 having a single arm 106, the surgical manipulator assembly includes multiple arms each having a surgical tool. Each of the surgical tools can be inserted into separate access ports. The processor can control a powered joint of either of the multiple arms to backdrive the base. When the powered joint of one of the arms is being driven, joints of the other arm are locked so that the torque from the driven powered joint does not cause motion of the other arm.

In some examples, the powered joint 114 may drive the base 110 toward the optimal base location envelope 122 before the surgery is performed. However, the powered joint 114 may also drive the base 110 during the surgery. The powered joint 114 may reposition the base 110 multiple times throughout a procedure.

While FIGS. 6G and 6H show that a second repositioning of the base 110 can occur due to a new obstacle 612 entering the vicinity of the base 110, in some implementations, other or additional parameters can change that can result in the processor 302 determining that a second repositioning of the base 110 may be beneficial. In some implementations, different surgical tools can result in different workspace requirements. As a result, if a surgical tool is "switched" with another surgical tool (e.g., the surgical tool dismounted from the arm and a different surgical tool mounted onto the arm) during the surgery, the processor 302 can detect that the surgical tool has been switched and compute a new optimal base location envelope. If the base of the surgical manipulator assembly is not within the new optimal base location envelope for the currently mounted, different surgical tool, after the surgical tool has been switched, the processor 302 can control the powered joint 114 to reposition the base 110 in light of the different surgical tool.

In some cases, the remotely controllable arm 106 is subject to an external force during the surgery that causes the base 110 to shift from its position. The pose sensors 309 can detect articulation about the joints 150a-150c and 156a-156g due to the external force or can detect movement of the base 110 due to the external force. Due to the movement of the components of the surgical manipulator assembly 104, the processor 302 may determine that the base 110 may need to be backdriven and be repositioned again toward the optimal base location envelope 122.

In some examples, the distal portion of the arm 106 (or of a cannula or surgical tool 108 or other item mounted to the arm 106) may be moved from one access port to another access port during the surgery. For example, when the distal portion of the arm 106 (or of a cannula or surgical tool 108 or other item mounted to the arm 106) is moved to the new access port, the processor 302 can control the powered joint 114 to backdrive the base 110 for a second time. Because the new access port may be positioned in a different area on the patient 102, the extent of the workspace necessary for the surgical tool 108 to perform the surgical procedure may change as well. Thus, before or after placement of the surgical tool 108 in the new access port, the operator may demonstrate a new extent of the workspace. With these changes in both the position of the access port (e.g., the port data 514) and the extent of the workspace (e.g., the procedure data 504), the processor 302 may compute new values for the indices of the current pose of the remotely controllable arm 106 and control the powered joint 114 to backdrive the base 110 for a second time in light of these new index values.

While demonstration of the workspace has been described herein as including a physical movement of the distal portion of the arm 106 (or of a cannula or surgical tool 108 or other item mounted to the arm 106) through the workspace, in some examples, the operator can demonstrate the workspace without physically moving the distal portion of the arm 106 (or of a cannula or surgical tool 108 or other item mounted to the arm 106). For example, the operator may graphically indicate on a display the extent of the workspace. The operator can specify the extent of the workspace using a computing device with a touchscreen display. By operating the touchscreen display, the operator can delineate the extent of the workspace. The computing device can deliver an input indicative of the extent of the workspace to the processor 302. In some examples, the operator can use a physical tool that can be detected by a sensor on the surgical manipulator assembly 104. The physical tool can be a hand or a pointing device that can demarcate the workspace. The sensor can, for example, optically detect the position of the physical tool and then generate signals for the processor 302, which in-turn determines extent of the workspace based on the sensor signals.

While the remotely controllable arm 106 is described as being mounted to the cart 111, in some implementations, the remotely controllable arm may be attached to a stationary or a movable table. Referring to the example depicted in FIG. 9A, a wheeled robotic table system 900A includes a table base 902A. A remotely controllable arm 904A includes an arm base 906A movably attached to the table base 902A. For example, the arm base 906A may be attached to the table base 902A at a prismatic joint 908A that allows the arm base 906A to translate along the table base 902A. In some implementations, the arm base 906A is attached to the table base 902A at a rotational joint that allows the arm base 906A to rotate about the table base 902A. In other examples, various remotely controllable arms (e.g. arm 904A) are designed to be attached to different portions of a table system (e.g. table system 900A). Example attachment portions include a base of the table system, a surface of the table system, one or more rails proximate to the table surface (if such rails exist), etc. In some implementations, the arm base 906A is removably attached to the table base 902A, and may be removed when not to be used in the operation. In some implementations, the arm 904A is folded under the table surface when not to be used in the operation.

Figure 9A:
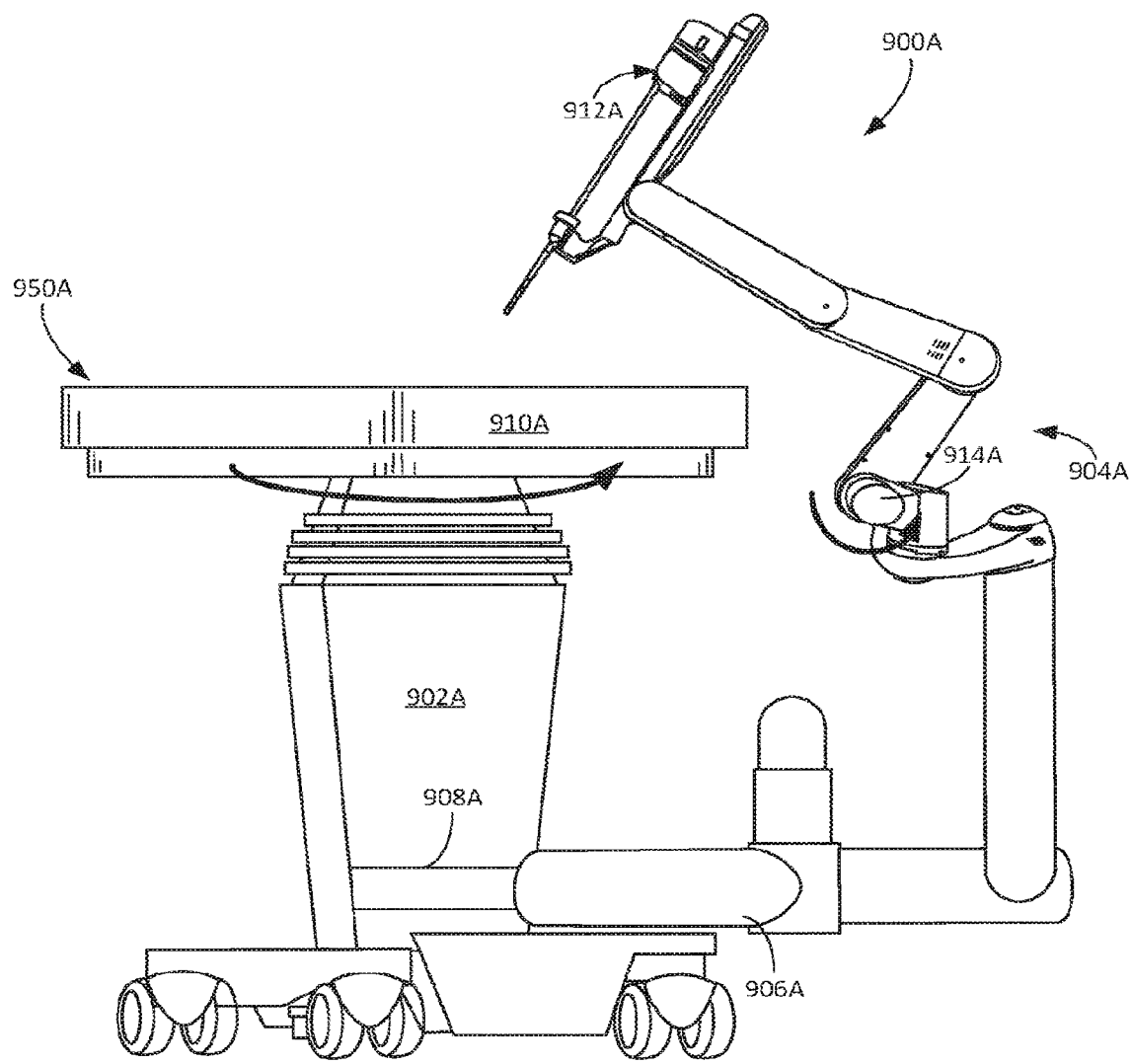
FIG. 9A is a perspective view of an example robotic table system.

In the FIG. 9A example, a table surface 910A is positioned on the table base 902A and is movable relative to the table base 902A. For example, the table surface 910A may be pivoted about the table base 902A or rotated about the table base 902A.

Before a surgery is performed, the processor can control an actuator coupled to the table surface 910A to cause the table surface 910A to move relative to the table base 902A while a position and/or orientation of surgical tool 912A is maintained. The processor 302 can also backdrive the arm base 906A relative to the table base 902A using a powered joint 914A. In this regard, the processor can control the position of the table surface 910A and control the position of the arm base 906A while the position and/or orientation of a distal portion of arm 804A (or an item supported by the arm such as a cannula or the surgical tool 912A) is maintained. The processor can determine a combination of an optimum table surface location and an optimum arm base location based on the indices described herein.

The table system 900A shown in FIG. 9A includes a plurality of wheels that allow the table system 900A to be repositioned with respect to a separately movable surgical manipulator assembly (e.g., surgical manipulator assembly 104), or to be moved around the operating area or from room to room, etc.

Figure 9B:
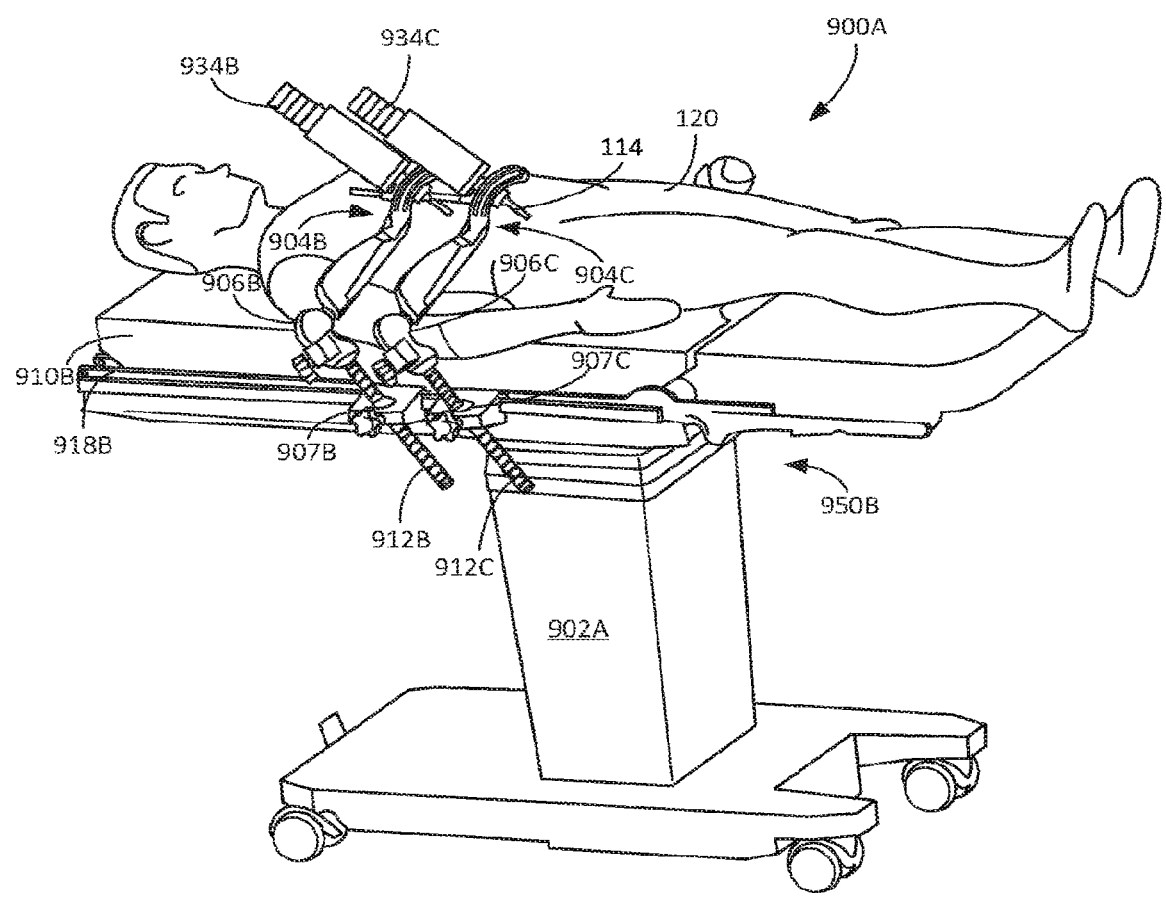
FIG. 9B is a perspective view of another example controllable arm.

FIG. 9B is a perspective view of another example controllable arm that may be attached to a stationary or movable table. A wheeled table 950B includes a table base 902B. A table surface 910B is positioned on the table base 902B. The table surface 910B can be used to support a work piece such as patient 920B, cadaver, body part, or a non-human work piece. In the example shown in FIG. 9B, two remotely controllable arms 904B, 904C includes arm bases 906B, 906C that may be removably attached to a number of different locations along a table rail 918B. During operation, the controllable arms 904B, 904C are driven to move tools 934B, 934C within associated workspaces. In some implementations, the controllable arms 904B, 904C are teleoperable and include remotely operable powered joints that, when driven, reposition and reorient the tools 934B,C with respect to the workspace. In some implementations, and like the other remotely controllable arms described herein, the controllable arms 904B, 904C can also be operated directly through input applied directly on the links or joints of the controllable arms 904B, 904C, allowing direct operator manipulation of the controllable arms 904B, 904C.

Similar to what has been described for the robotic table system 900A, before a surgery is performed, the processor 302 can operate an actuator to cause the table surface 910B to move relative to the table base 902B. The processor 302 may also operate one or more powered joints of the arms 904B, 904C to reposition the arm bases 906B, 906C relative to the table rail 918B. For example, the arm bases 906B, 906C, with passive joints 907B, 907C that are lockable to the table rail 918B, can be backdriven to move along the table rail 918B. As a result, the passive joints 907B, 907C and the arm bases 906B, 906C can be jointly moved or slid along the table rail 918B. As described herein, during this repositioning, the positions and/or orientations of distal portions of the arms 904B, 904C are maintained.

In some implementations, the arm bases 906B, 906C are movable relative to the tools 934B, 934C in manners other than sliding along the table rail 918B. The repositioning of the passive joints 907B, 907C with the arm bases 906B, 906C relative to the table rail 918B corresponds to a first repositioning, and the arm bases 906B, 906C are further repositioned relative to the passive joints 907B, 907C in a second repositioning. For example, links 912B, 912C coupled to the arm bases 906B, 906C can be movable relative to the passive joints 907B, 907C in insertion motions or roll motions, thereby causing relative translation or reorientation of the arm bases 906B, 906C and the tools 934B, 934C. The one or more powered joints of the arms 904A, 904B can be operated to backdrive the arm bases 906B, 906C with the links 912B, 912C to move relative to the passive joints 907B, 907C. As described herein, during this second repositioning, the positions and/or orientations of distal portions of the arms 904B, 904C are maintained.

The obstacle data 510 is described as being indicative of locations of obstacles in the workspace. While obstacles are described as including equipment in the workspace, other obstacles are possible. In some implementations, the obstacle data 510 include data indicative of obstacles include expected locations of any operators in the surgical environment 10, uneven floor surfaces, or other obstacles in the workspace that may impede movement of the base 906B, 906C or the remotely controllable arm 106. In some implementations, referring back to FIG. 9B, the obstacle data 510 include data indicative of the locations of the ends of the table rail 918B relative to the locations of the arm bases 906B, 906C. The processor directs the manual repositioning based on locations of the ends of the table rail 918B to avoid directing the operator to move the arm bases 906B, 906C beyond their allowable ranges of motion along the table rail 918B. Because the passive joints 907B, 907C are configured to be locked to the table rail 918B to support the arm bases 906B, 906C and hence the arms 904B, 904C above the table surface 910B, the ends of the table rail 918B limit the ranges of motion of the passive joints 907B, 907C and hence the arm bases 906B, 906C. The processor can backdrive the arm bases 906B, 906C so that the passive joints 907B, 907C are not driven beyond their allowable range of motion.

Figure 10A:
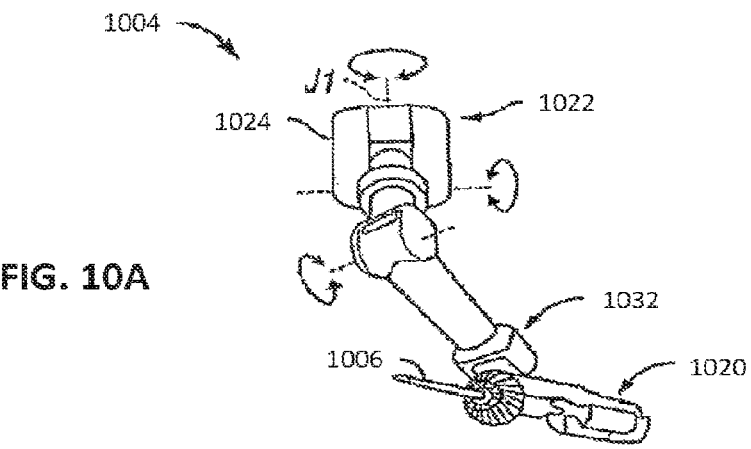
FIGS. 10A-10C are bottom, side, and back views of a controllable arm having a range of joint states for a given end effector position.
Figure 10B:
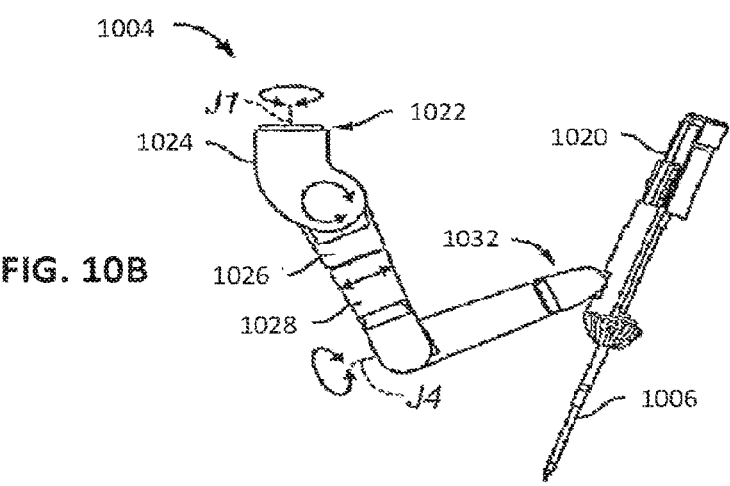
Figure 10C:
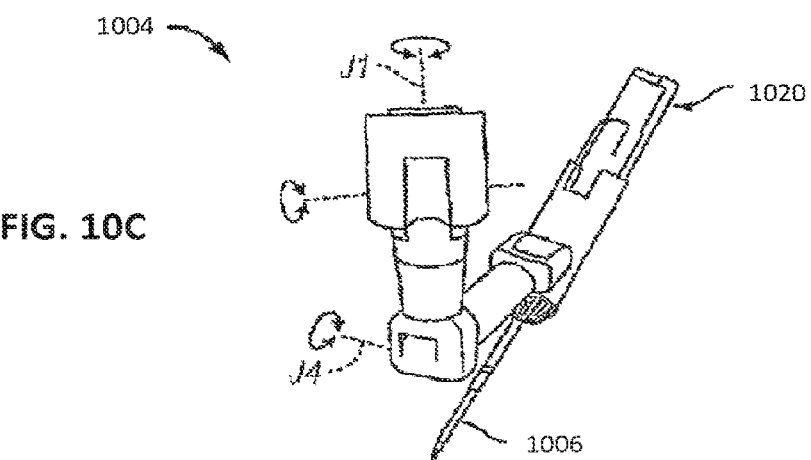

The remotely controllable arm 106 and 904A, 904 B, 904C, as described herein, are examples of types of robotic manipulator arm assemblies envisioned within the scope of this disclosure. FIGS. 10A-10C depict bottom, side, and back views of another example robotic manipulator arm assembly 1004 (also referred to as remotely controllable arm 1004). Implementations of remotely controllable arms include the examples described herein as well as combinations of joint and linkage configurations describes with respect to the remotely controllable arms 106, 904A,B,C, and 1004.

In some implementations, the remotely controllable arm 1004 is be coupled with a surgical instrument 1006 to affect movements of the instrument 1006 relative to a base 1002. As a number of different surgical instruments having differing end effectors may be sequentially mounted on each remotely controllable arm 1004 during a surgical procedure (typically with the help of a surgical assistant), an instrument holder 1020 will preferably allow rapid removal and replacement of the mounted surgical instrument 1006.

The example remotely controllable arm 1004 is mounted to the base 1002 by a pivotal mounting joint 1022 so as to allow the remainder of remotely controllable arm 1004 to rotate about a first joint axis J1, with the first joint 1022 providing rotation about a vertical axis in the exemplary implementation. Base 1002 and first joint 1022 generally include a proximal portion of remotely controllable arm 1004, with the manipulator extending distally from the base toward instrument holder 1020 and end effector 1050.

Figure 10D:
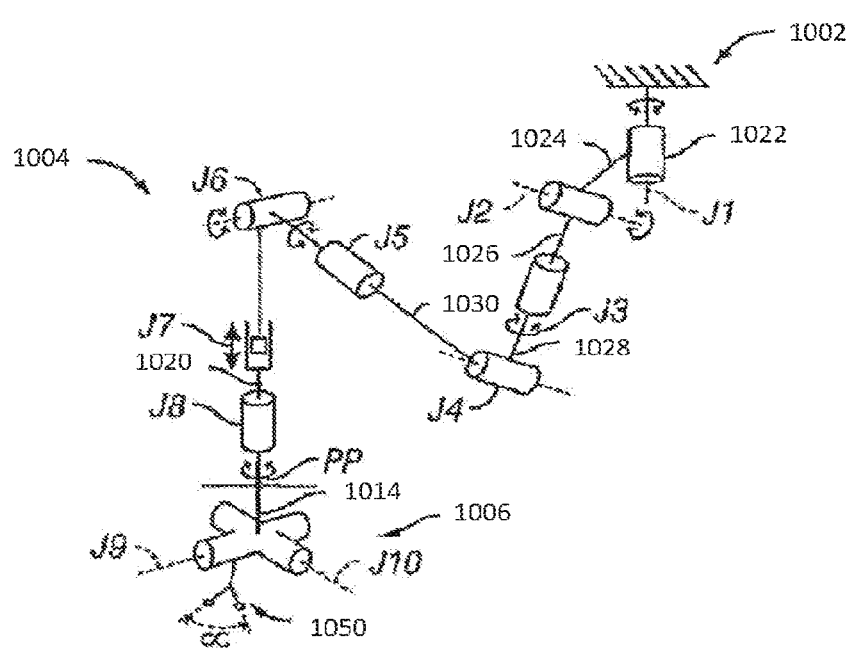
FIG. 10D is a schematic diagram illustrating the degrees of freedom of the controllable arm of FIGS. 10A-10C.

Describing the individual links of the controllable arm 1004 as illustrated in FIGS. 10A-10C, along with the axes of rotation of the joints connecting the links as illustrated in FIG. 10D, a first link 1024 extends distally from base 1002 and rotates about first pivotal joint axis J1 at joint 1022. Many of the remainder of the joints can be identified by their associated rotational axes in FIG. 10D. For example, a distal end of first link 1024 is coupled to a proximal end of a second link 1026 at a joint providing a horizontal pivotal axis J2. A proximal end of a third link 1028 is coupled to the distal end of the second link 1026 at a roll joint so that the third link generally rotates or rolls at joint J3 about an axis extending along and, in some cases, aligned with axes of both the second and third links. Proceeding distally, after another pivotal joint J4, the distal end of a fourth link 1030 is coupled to instrument holder 1020 by a pair of pivotal joints J5, J6 that together define an instrument holder wrist 1032. A translational or prismatic joint J7 of the remotely controllable arm 1004 facilitates axial movement of instrument 1006 and the elongate shaft 1014 of the instrument 1006 through the minimally invasive aperture, and also facilitates attachment of the instrument holder 1020 to a cannula through which the instrument 1006 is slidably inserted.

Distally of instrument holder 1020, the surgical instrument 1006 may include additional degrees of freedom. Actuation of the degrees of freedom of the surgical instrument 1006 will often be driven by motors of the remotely controllable arm 1004. Alternative implementations may separate the surgical instrument 1006 from the supporting manipulator arm structure at a quickly detachable instrument holder/instrument interface so that one or more joints shown here as being on the surgical instrument 1006 are instead on the interface, or vice versa. In other words, the interface between the surgical instrument 1006 and remotely controllable arm 1004 may be disposed more proximally or distally along the kinematic chain of the manipulator arm assembly 1004 (which may include both the surgical instrument and the manipulator arm assembly 1004). In the exemplary implementation, the surgical instrument 1006 includes a rotational joint J8 proximally of the pivot point PP, which generally is disposed at the site of a minimally invasive aperture. A distal wrist of the surgical instrument 1006 allows pivotal motion of end effector 1050 about instrument wrist joint axes J9, J10. An angle α between end effector jaw elements may be controlled independently of the end effector 1050 location and orientation. In some implementations, one or more of the joints shown in FIGS. 10A-10D are controlled to drive the end effector 1050. In some implementations, one or more of the joints shown in FIGS. 10A-10D, using the methods described herein, are controlled to backdrive the base 1002 to reposition the base 1002.

Figure 11:
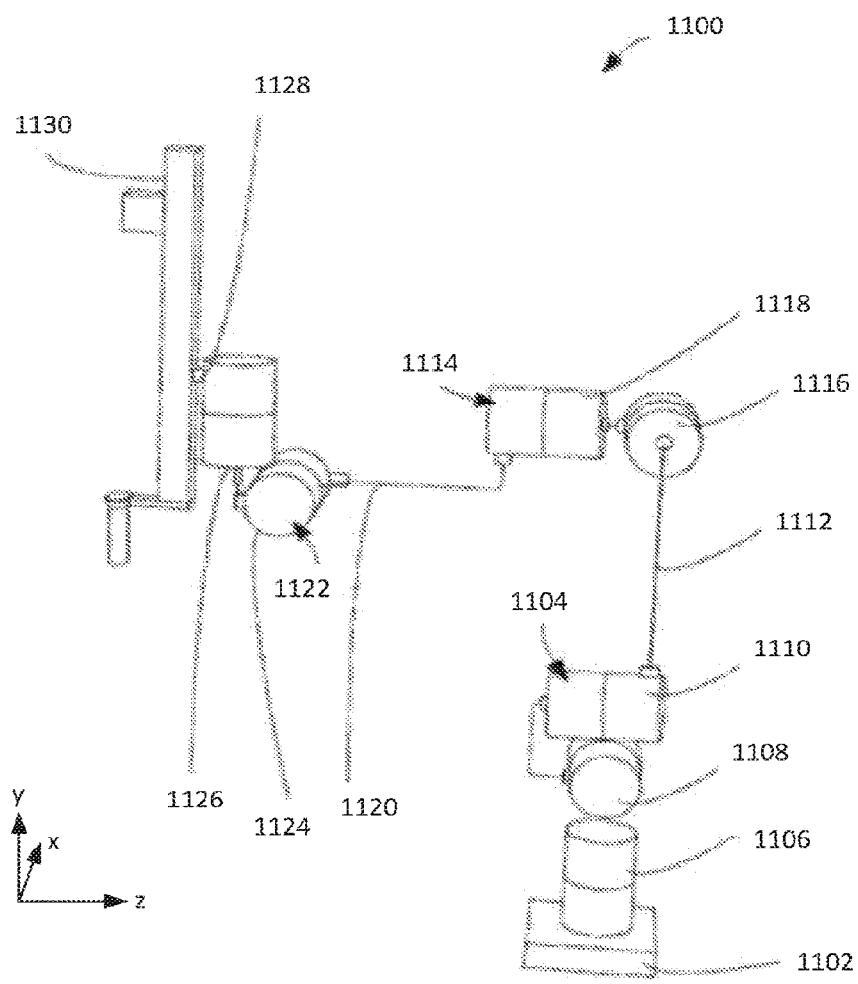
FIG. 11 is a schematic diagram illustrating degrees of freedom of another example of a controllable arm.

In another example, referring to FIG. 11, a controllable arm 1100 that may be made remotely controllable includes a base 1102 connected to a joint system 1104. A link 1112 connects the joint system 1104 to a joint system 1114, and a link 1120 connects the joint system 1114 to the joint system 1122. In some implementations, a joint 1106 rotates a portion of the remotely controllable arm 1100 that is distal to the base 1102 in a rotation relative to the base 1102, e.g., about the y-axis. In some implementations, a joint 1128 translates an instrument holder 1130 relative to joint system 1122, e.g., along the y-axis. Each joint and joint system is, for example, selectively operable to cause relative movement between portions of the remotely controllable arm 1100, e.g., translation and/or rotation between portions of the remotely controllable arm 1100.

The joint system 1104 is operable to cause relative rotation between the link 1112 and the joint system 1104. The joint system 1104 includes, for example, a first rotatable joint 1108 and a second rotatable joint 1110. The first joint 1108, when driven, causes relative rotation between the first joint 1108 and the second joint 1110, e.g., about the x-axis. The second joint 1110, when driven, causes relative rotation between the link 1112 and the second joint 1110, e.g., about the z-axis. The joint system 1114 is operable to cause relative rotation of the link 1120 and the joint system 1114. The joint system 1114, for example, includes a first joint 1116 and a second joint 1118. The first joint 1116, when driven, causes relative rotation between the first joint 1116 and the second joint 1118, e.g., about the x-axis. The second joint 1118, when driven, causes relative rotation between the second joint 1118 and the link 1120. The joint system 1122 is operable to cause relative rotation between the instrument holder 1130 and the joint system 1122. The joint system 1122 includes, for example, a first joint 1124 and a second joint 1126. The first joint 1124, when driven, causes relative rotation between the first joint 1124 and the second joint 1126, e.g., about the x-axis. The second joint 1126, when driven, causes relative rotation between the second joint 1126 and the instrument holder 1130, e.g., about the y-axis. In some implementations, one or more of the joints shown in FIG. 11 are controlled to drive an end effector of an instrument held in the instrument holder 1130. In some implementations, one or more of the joints shown in FIG. 11, using the methods described herein, are controlled to backdrive the base 1102 to reposition the base 1102.

The remotely controllable arms 106, 904A,B,C, 1004, and 1100 are examples of remotely controllable arms. In some implementations, a remotely controllable arm includes a combination of joints in the examples of remotely controllable arms described herein. In this regard, in some implementations, a remotely controllable arm includes combinations of prismatic joints, rotational joints, and joint systems other than the combinations shown with respect to the remotely controllable arms 106, 904A,B,C, 1004, and 1100.

The surgical systems (e.g., the surgical system 100) and robotic components of the surgical systems (e.g., the remotely controllable arm 106, the surgical manipulator assembly 104) described herein can be controlled, at least in part, using one or more computer program products, e.g., one or more computer programs tangibly embodied in one or more information carriers, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment.

Operations associated with controlling the surgical systems described herein can be performed by one or more programmable processors executing one or more computer programs to perform the functions described herein. Control over all or part of the surgical systems described herein can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer include one or more processors for executing instructions and one or more storage area devices for storing instructions and data. Generally, a computer will also include, or be operatively coupled to receive data from, or transfer data to, or both, one or more machine-readable storage media, such as mass PCBs for storing data, e.g., magnetic, magneto-optical disks, or optical disks. Machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

What is claimed is:

1. A robotic system comprising:
a base movable relative to a floor surface;
a robotic arm extending from the base and comprising a powered joint operable to move a distal portion of the robotic arm, the robotic arm configured to support a tool; and
a processor communicatively coupled to the robotic arm, the processor configured to:
receive input data indicative of a characteristic of an access port through which the tool is insertable to perform a procedure on a subject, wherein the input data is further indicative of a second characteristic of a second access port, the second access port to be used in the procedure;
determine a desired position or orientation of the base using the input data, and
drive the powered joint to reposition the base toward the desired position or orientation.

2. The robotic system of claim 1, wherein:
the movable base is configured to be attached to a table on which the subject is positioned during the procedure; or
the robotic system further comprises a cart coupled to the base, wherein the cart is configured to roll on a floor.

3. The robotic system of claim 1, wherein:
the desired position or orientation of the base comprises both the desired position of the base and the desired orientation of the base.

4. The robotic system of claim 1, wherein:
the processor is further configured to receive information about the procedure, wherein the information about the procedure comprises an extent of a workspace for the procedure; and
the processor is configured to determine the desired position or orientation further using the information about the procedure.

5. The robotic system of claim 4, wherein the information about the procedure is indicative of a boundary of a workspace for the procedure.

6. The robotic system of claim 4, wherein the processor is configured to receive the input data by:
receiving a signal from a sensor indicative of movement of the robotic arm during an operator demonstration of a workspace for the procedure.

7. The robotic system of claim 6 wherein:
the robotic arm comprises a distal portion configured to support the tool;
the workspace for the procedure is a workspace for the distal portion or the tool; and
the processor is configured to determine the desired position or orientation of the base using the input data by: using the signal.

8. The robotic system of claim 1, wherein:
the characteristic of the access port comprises a location of the access port.

9. The robotic system of claim 1, wherein:
the access port is a first access port, and the desired position or orientation of the base is a first desired position or orientation of the base; and
the processor is further configured to:
determine a second desired position or orientation of the base using the input data, and
drive the powered joint to reposition the base toward the second desired position or orientation.

10. The robotic system of claim 1, wherein the processor is configured to drive the powered joint to reposition the base toward the desired position or orientation by:
driving the powered joint to reposition the base in response to detecting that a position of the distal portion of the robotic arm is externally maintained relative to the access port.

11. A method of operating a robotic system comprising a robotic arm extending from a base, the robotic arm comprising a powered joint operable to move a distal portion of the robotic arm and configured to support and move a tool, the method comprising:
receiving, by a processor, input data indicative of a characteristic of an access port through which the tool is insertable to perform a procedure on a subject, wherein the input data is further indicative of a second characteristic of a second access port, the second access port to be used in the procedure;
determining, by the processor, a desired position or orientation of the base of the robotic system using the input data, and
driving, by the processor, the powered joint of the robotic arm to reposition the base of the robotic system toward the desired position or orientation.

12. The method of claim 11, further comprising:
receiving information about the procedure, wherein the information about the procedure comprises an extent of a workspace for the procedure; and
determining the desired position or orientation further comprises: using the information about the procedure.

13. The method of claim 11, further comprising:
determining a second desired position or orientation of the base using the input data; and
driving the powered joint to reposition the base toward the second desired position or orientation.

14. The method of claim 11, wherein driving the powered joint to reposition the base toward the desired position or orientation comprises:

driving the powered joint to reposition the base in response to detecting that a position of the distal portion of the robotic arm is externally maintained relative to the access port.

15. A non-transitory machine-readable medium comprising a plurality of machine-readable instructions which when executed by one or more processors associated with a robotic system comprising a robotic arm extending from a base, the robotic arm comprising a powered joint operable to move a distal portion of the robotic arm and configured to support and move a tool, are adapted to cause the one or more processors to perform a method comprising:

receiving input data indicative of a characteristic of an access port through which the tool is insertable, wherein the input data is further indicative of a second characteristic of a second access port;

determining a desired position or orientation of the base of the robotic system using the input data, and driving the powered joint of the robotic arm to reposition the base of the robotic system toward the desired position or orientation.

16. The non-transitory machine-readable medium of claim 15, wherein:

the method further comprises: receiving procedure data indicative of a procedure to be performed on a subject by the robotic system using the tool inserted through the access port; and determining the desired position or orientation further comprises: using the procedure data.

* * * * *